US010660822B2

United States Patent
Noguchi

(10) Patent No.: US 10,660,822 B2
(45) Date of Patent: May 26, 2020

(54) ADAPTER

(71) Applicant: JMS CO., LTD., Hiroshima-shi, Hiroshima (JP)

(72) Inventor: Yusuke Noguchi, Hiroshima (JP)

(73) Assignee: JMS CO., LTD., Hiroshima (JP)

(*) Notice: Subject to any disclaimer, the term of this patent is extended or adjusted under 35 U.S.C. 154(b) by 279 days.

(21) Appl. No.: 15/559,772

(22) PCT Filed: Mar. 18, 2016

(86) PCT No.: PCT/JP2016/058787
§ 371 (c)(1),
(2) Date: Sep. 19, 2017

(87) PCT Pub. No.: WO2016/152801
PCT Pub. Date: Sep. 29, 2016

(65) Prior Publication Data
US 2018/0064605 A1  Mar. 8, 2018

(30) Foreign Application Priority Data

Mar. 23, 2015 (JP) ................................. 2015-060038
Nov. 5, 2015 (JP) ................................. 2015-217564

(51) Int. Cl.
*A61J 1/20* (2006.01)
*A61M 5/162* (2006.01)
*A61M 39/14* (2006.01)

(52) U.S. Cl.
CPC ............... *A61J 1/2006* (2015.05); *A61J 1/20* (2013.01); *A61J 1/2048* (2015.05); *A61M 5/162* (2013.01); *A61M 39/14* (2013.01); *A61J 1/2096* (2013.01)

(58) Field of Classification Search
CPC ........ A61J 1/2006; A61J 1/201; A61J 1/2013; A61J 1/2017; A61J 1/2048; A61J 1/2051;
(Continued)

(56) References Cited

U.S. PATENT DOCUMENTS

2009/0216212 A1* 8/2009 Fangrow, Jr. ......... A61J 1/2096
604/406
2010/0176584 A1 7/2010 Ito et al.
(Continued)

FOREIGN PATENT DOCUMENTS

CN          101677905       3/2010
GB          2 352 051       1/2001
(Continued)

OTHER PUBLICATIONS

Office Action issued in corresponding Chinese Patent Application No. 201680016306.3, dated Nov. 4, 2019, 13 pages with translation.

*Primary Examiner* — Philip R Wiest
(74) *Attorney, Agent, or Firm* — Hamre, Schumann, Mueller & Larson, P.C.

(57) ABSTRACT

An arm (20) that faces a male member (10) is provided with a claw (30) that protrudes toward the male member (10). An adapter (1) can be connected to a female connector with the male member being inserted into the female connector and the claw engaging with the female connector. The arm is elastically deformable so that the claw can move away from the male member. The claw includes a slidable portion (33a) that slides on the female connector during a process in which the adapter is connected to the female connector. The slidable portion moves the claw in a direction away from the male connector while the slidable portion slides on the female connector. A contour shape of the slidable portion seen in a direction that is orthogonal to a central axis (1a) that passes through the male member includes a smooth convex curve.

4 Claims, 19 Drawing Sheets

(58) Field of Classification Search
CPC ...... A61J 1/2055; A61J 1/2065; A61J 1/2072;
A61J 1/2075; A61J 1/2079; A61J 1/2082;
A61J 1/2086; A61J 1/2089; A61J 1/2093;
A61J 1/2096
See application file for complete search history.

(56) References Cited

U.S. PATENT DOCUMENTS

2012/0179129 A1    7/2012   Imai
2015/0265499 A1    9/2015   Takeuchi

FOREIGN PATENT DOCUMENTS

| JP | 2003-513709 | 4/2003 |
|----|-------------|--------|
| JP | 2006-526477 | 11/2006 |
| JP | 2011-512205 | 4/2011 |
| JP | 2014-079355 | 5/2014 |
| WO | 01/06288 | 1/2001 |
| WO | 01/34089 | 5/2001 |
| WO | 2004/108058 | 12/2004 |
| WO | 2009/105489 | 8/2009 |
| WO | 2011/068190 | 6/2011 |

\* cited by examiner

ADAPTER

TECHNICAL FIELD

The present invention relates to an adapter that is provided with: a male member that can be inserted into a female connector (e.g. a plug member of a vial bottle); and a claw that can engage with the female connector when the male member is inserted into the female connector.

BACKGROUND ART

Vial bottles in which a powdered drug is enclosed in an airtight manner are widely available. When such a drug is given to a patient, a solvent is injected into a vial bottle to dissolve the drug so that a drug solution can be obtained, and then the drug solution is transferred from the vial bottle to a drug solution bag. To inject a solvent into a vial bottle or take a drug solution out of a vial bottle, a plug member (a rubber plug) that seals the mouth (the opening) of the vial bottle is pierced with a puncture needle (also referred to as "a bottle needle").

A drug that is enclosed in a vial bottle may be a drug specified as a powerful drug such as an anticancer drug. It is necessary to avoid situations in which such a dangerous drug or a solution thereof adheres to a worker's finger or the like, and situations in which a worker breathes in the drug or vapor therefrom. Therefore, in order to prevent a puncture needle that pierces through a plug member of a vial bottle from unintentionally coming out of the plug member, an adapter in which claws, which engage with a flange that has an expanded diameter and surrounds the mouth of a vial bottle (or an aluminum cap that covers the flange), are provided integrally with a puncture needle is often used.

Patent Document 1 discloses an example of such an adapter. In an adapter 900 according to Patent Document 1, as shown in FIG. 12, claws 930 that protrude toward a puncture needle 910 are provided at leading end portions of arms 920 that face the puncture needle 910. The arms 920 are elastically bendable so that the claws 930 can be displaced in radial directions so as to move away (outward) from the puncture needle 910. Upon the adapter 900 being pressed toward the plug member of the vial bottle, the puncture needle 910 starts piercing the plug member, and, in tandem with that, slidable portions 933a of the claws 930 abut against an edge of an aluminum cap of the vial bottle. The slidable portions 933a slide on the aluminum cap as the puncture needle 910 enters into the plug member. Since the slidable portions 933a are inclined, the claws 930 are displaced outward away from the puncture needle 910 while the slidable portions 933a slide on the aluminum cap. Upon the claws 930 having moved past the aluminum cap, the arms 920 elastically return to their original shape, and the claws 930 engage with the flange. In this way, it is possible to pierce the plug member with the puncture needle 910 and engage the claws 930 with the flange by simply pressing the adapter 900 toward the vial bottle.

PRIOR ART DOCUMENTS

Patent Document

[Patent Document 1] JP 2014-79355A

DISCLOSURE OF INVENTION

Problem to be Solved by the Invention

During a process in which the adapter 900 is connected to the vial bottle, the force with which the adapter 900 is pressed toward the vial bottle acts to displace the claws 930 outward while sliding the claws 930 over the aluminum cap. With conventional adapters, there is the problem that it is necessary to apply a significantly large force to the adapter 900 when displacing the claws 930. In particular, in the case of connecting the adapter 900 to a vial bottle that has an aluminum cap with a larger outer diameter, it is necessary to apply an even greater force to the adapter 900 because the claws 930 needs to be further displaced, and it can be practically difficult to connect the adapter 900 to the vial bottle. In such a case, if the adapter 900 is forcibly pressed toward the vial bottle, the direction in which the force is applied inclines, and accordingly the adapter 900 inclines relative to the vial bottle, which may result in a situation in which a dangerous drug leaks to the outside via a narrow gap between the puncture needle and a hole in the plug member pierced by the puncture needle.

The present invention aims to solve the above-described conventional problem, and to provide an adapter that can be connected to a female connector without the need to apply a large force.

Means for Solving Problem

An adapter according to the present invention comprise: a male member; an arm that faces the male member; and a claw that is provided on the arm so as to protrude toward the male member. The adapter is configured to be connected to a female connector with the male member being inserted into the female connector and the claw engaging with the female connector. The arm is elastically deformable so that the claw can move away from the male member. The claw includes a slidable portion that slides on the female connector during a process in which the adapter is connected to the female connector. The slidable portion is configured to move the claw in a direction away from the male connector while the slidable portion slides on the female connector. A contour shape of the slidable portion seen in a direction that is orthogonal to a central axis that passes through the male member includes a smooth convex curve.

Effects of the Invention

According to the present invention, the contour shape of the slidable portion includes a smooth convex curve. With this configuration, the force that is applied to the adapter toward the female connector can be effectively used to move the claw in a direction away from the male member. Therefore, it is possible to connect the adapter to the female connector without applying a large force to the adapter. Also, the range of diameters of female connectors to which the adapter can be connected is increased.

DESCRIPTION OF THE INVENTION

Figure 1A:
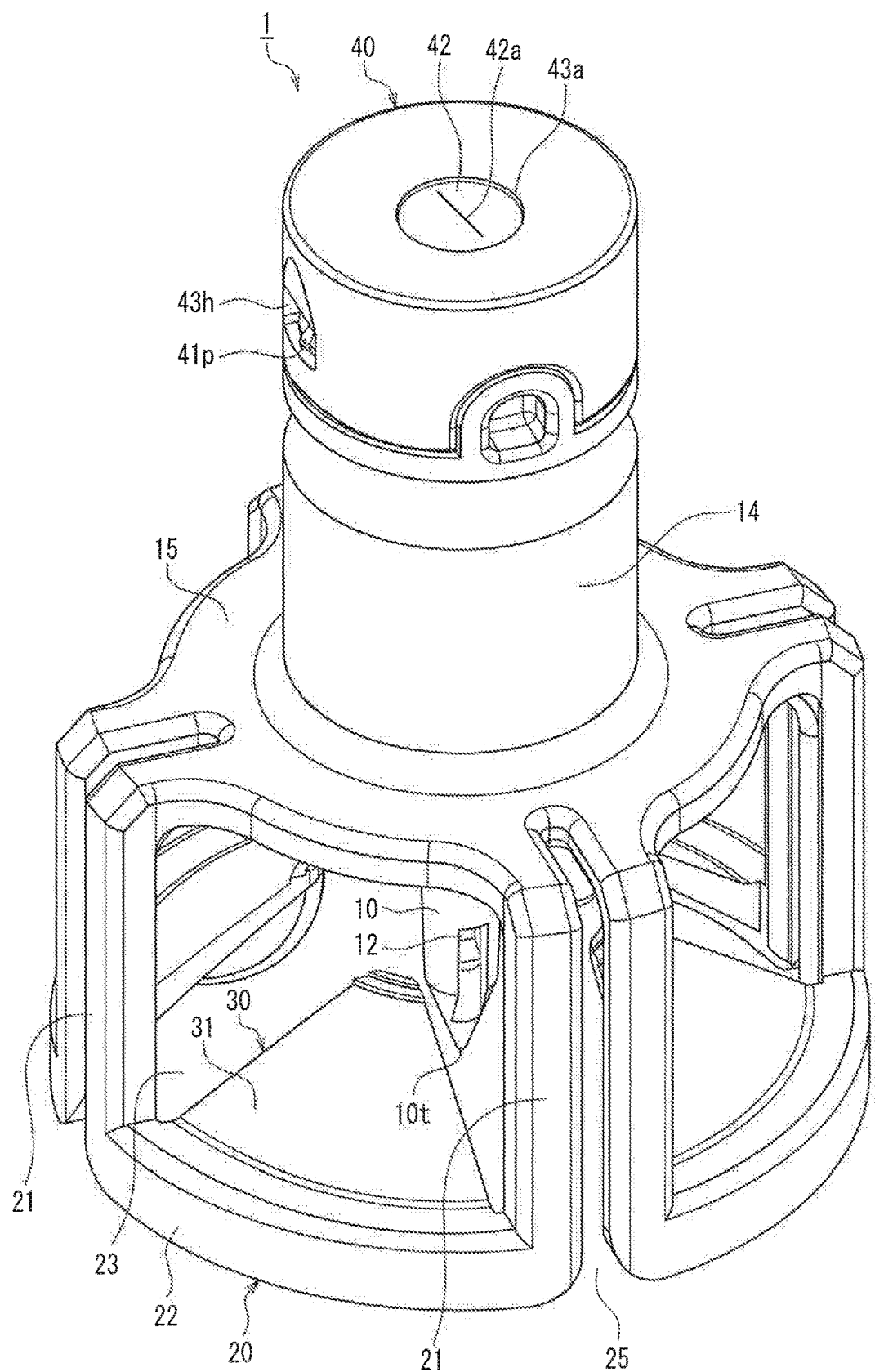
FIG. 1A is a perspective view showing an adapter according to Embodiment 1 of the present invention seen from above.

In the above-described adapter according to the present invention, the smooth convex curve may be an arc or a portion of an ellipse. With this configuration, it is possible to connect the adapter to a female connector with an even smaller force.

The slidable portion may be provided on a rib that extends along a plane that includes the central axis. Alternatively, the slidable portion may be provided on a rib that extends along a plane that is parallel with a plane that includes the central axis. With these respective configurations, it is possible to reduce a friction force between the slidable portion and the female connector, and therefore it is possible to connect the adapter to the female connector with an even smaller force.

The male member may be a puncture needle that has a sharp leading end. With this configuration, it is possible to provide an adapter that can be connected to a female connector that is sealed by a plug member such as a rubber plug.

The female connector may include a plug member of a vial bottle. In this case, the claw may engage with a flange that has an expanded diameter and surrounds the mouth of the vial bottle. With this configuration, it is possible to provide an adapter that can be connected to a vial bottle. Also, it is possible to provide an adapter that can be connected to vial bottles with a wide range of plug members and flanges in terms of diameter.

Hereinafter, the present invention will be described in detail by means of preferred embodiments. However, it goes without saying that the present invention is not limited to the following embodiments. In the drawings referenced in the following description, only the relevant members needed in order to describe the present invention among the members constituting the embodiment of the present invention are shown in a simplified manner for the sake of convenience in the description. Accordingly, the present invention can include any member that is not shown in the following drawings. Also, the members shown in the following drawings may be changed or omitted within the scope of the present invention. In the drawings shown below, identical members are denoted by identical reference signs, and redundant description thereof is not included.

Embodiment 1

Figure 1B:
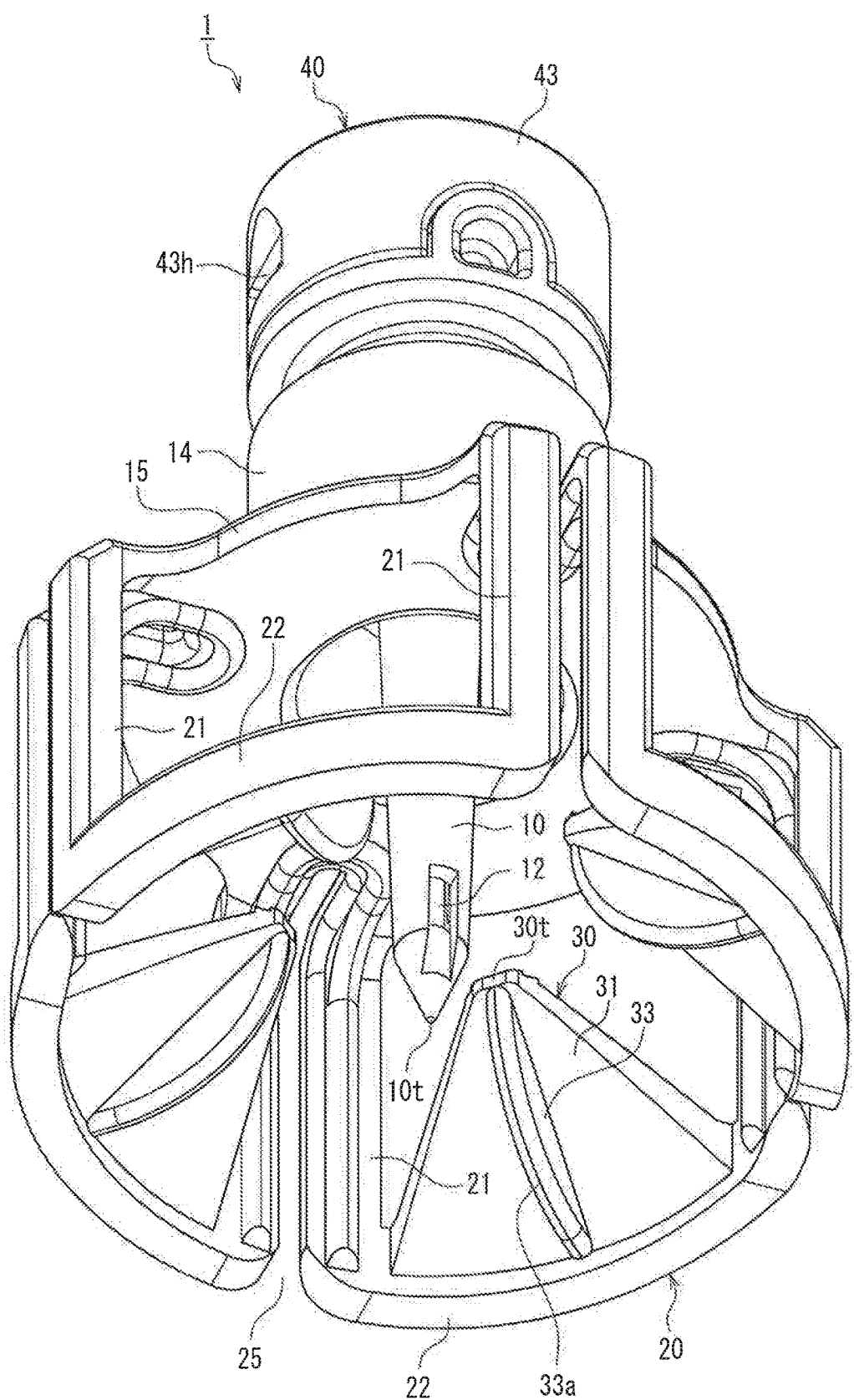
FIG. 1B is a perspective view showing the adapter according to Embodiment 1 of the present invention seen from below.
Figure 1C:
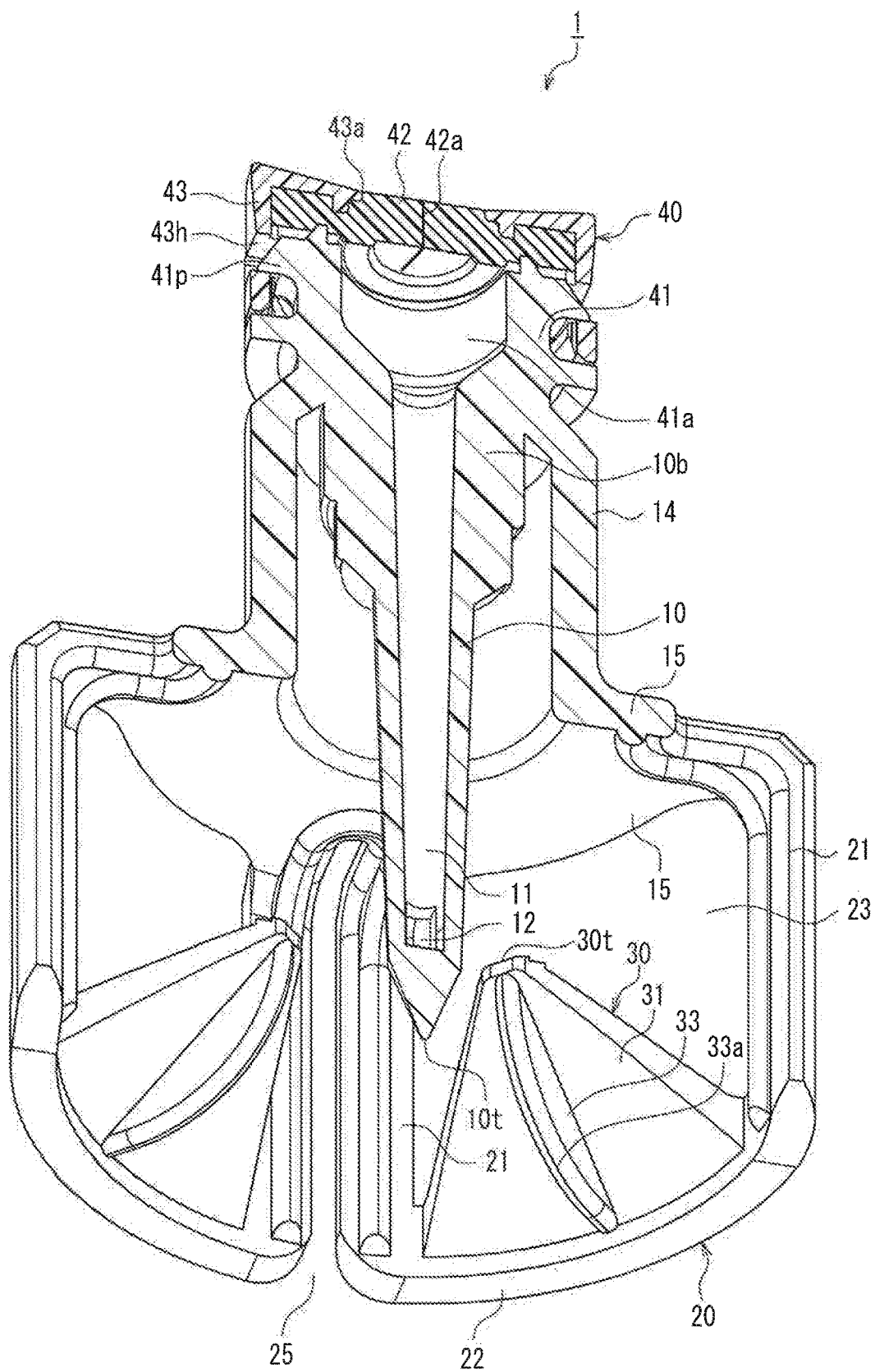
FIG. 1C is a cross-sectional perspective view showing the adapter according to Embodiment 1 of the present invention seen from below.
Figure 1D:
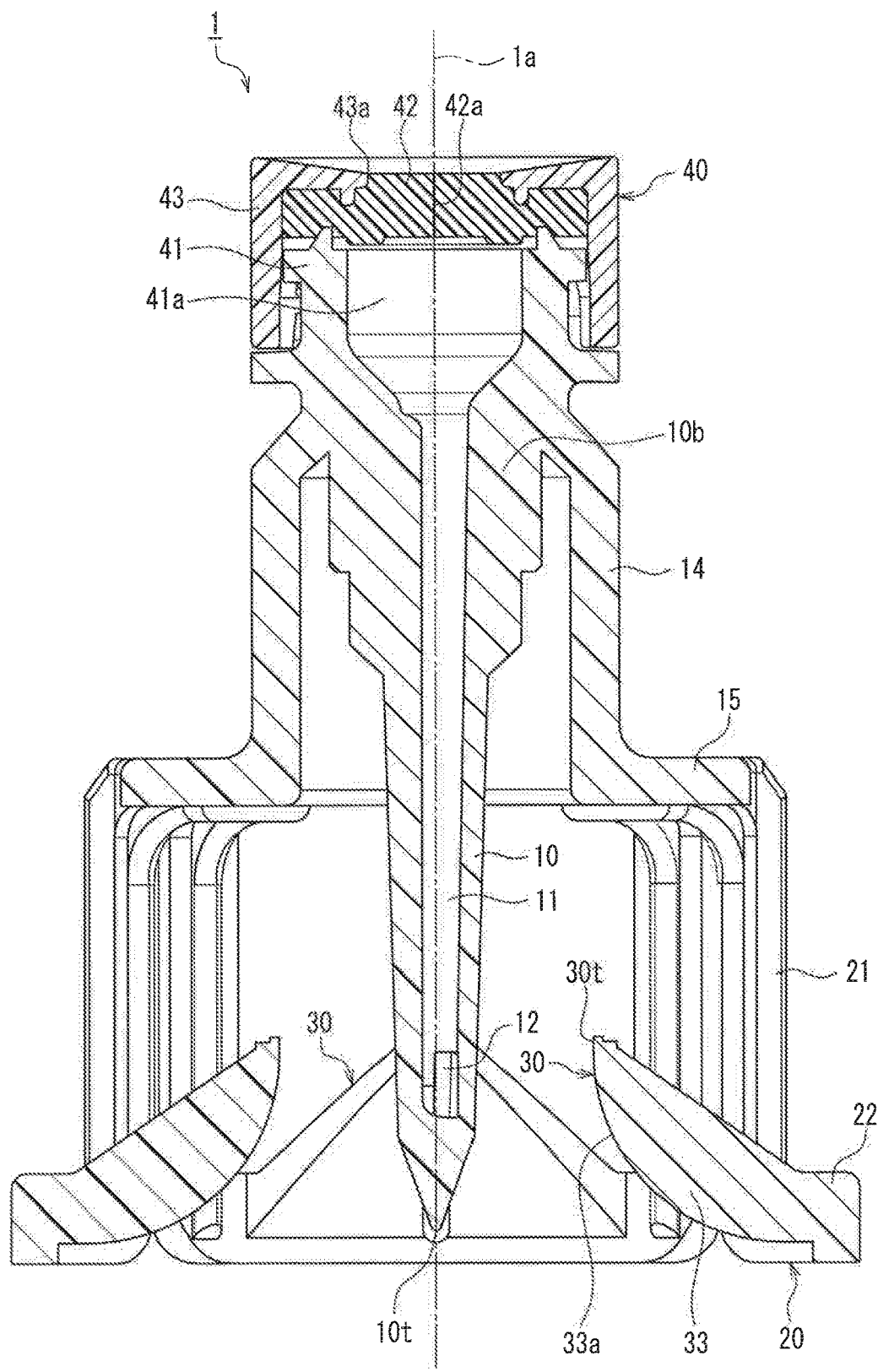
FIG. 1D is a cross-sectional view of the adapter according to Embodiment 1 of the present invention along a plane that includes a central axis and claws of the adapter.

FIG. 1A is a perspective view showing an adapter 1 according to Embodiment 1 of the present invention seen from above. FIG. 1B is a perspective view of the adapter 1 seen from below, FIG. 1C is a cross-sectional perspective view of the adapter 1 seen from below, FIG. 1D is a cross-sectional view of the adapter 1 along a plane that includes a central axis 1a and claws 30 of the adapter 1. For the sake of convenience in the following description, a direction in which the central axis 1a extends is referred to as "the vertical direction", and a direction that is parallel with a plane that is orthogonal to the central axis 1a is referred to as "the horizontal direction". The terms "above" and "below" relative to the adapter 1 are defined based on the orientation (the position) of the adapter 1 shown in FIGS. 1A to 1D. A direction in which a straight line that intersects the central axis 1a at right angles extends is referred to as "a radial direction", and a rotational direction about the central axis 1a is referred to as "the circumferential direction". In a radial direction, the side closer to the central axis 1a is referred to as "the inside", and the side farther from the central axis 1a is referred to as "the outside". However, "the vertical direction", "above", "below", and "the horizontal direction" are not intended to mean the orientation of the adapter 1 in actual use.

The adapter 1 is provided with a puncture needle (a male member) 10 that extends along the central axis 1a. The puncture needle 10 is provided with a sharp leading end 10t at the lower end thereof. A flow channel 11 through which liquid (e.g. a drug solution) flows is formed inside the puncture needle 10. The flow channel 11 communicates with an opening 12 that is provided in an outer circumferential surface of the puncture needle 10 near the leading end 10t.

As shown in FIGS. 1C and 1D, a tubular portion 14 surrounds a portion of the puncture needle 10 near a base end portion 10b of the puncture needle 10. The tubular portion 14 has a hollow circular cylinder shape, is located coaxially with the puncture needle 10, and is separated from the puncture needle 10. The upper end of the tubular portion 14 is connected to the base end portion 10b of the puncture needle 10. A top plate 15 protrudes outward from the lower end of the tubular portion 14 in radial directions. The top plate 15 is a flat plate that is substantially orthogonal to the central axis 1a. As shown in FIGS. 1A and 1B, four arms 20 extend downward from the outer peripheral edge of the top plate 15. Each arm 20 includes a pair of elastic portions 21 that extend downward from the top plate 15, and a bridge portion 22 that connects the bottom ends of the pair of elastic portions 21, and thus each arm 20 has a substantially "U" like shape overall. The bridge portion 22 has the shape of an arc of a circle that is centered around the central axis 1a when seen in a direction along the central axis 1a. The arms 20 and the top plate 15 define openings 23 that are surrounded thereby and that each have a substantially rectangular shape, and the puncture needle 10 inside the arms 20 can be seen through the openings 23.

In the present Embodiment 1, the tubular portion 14 is interposed between the base end portion 10b of the puncture needle 10 and the top plate 15. However, the present invention is not limited to such a configuration. For example, the tubular portion 14 may be omitted, and the puncture needle 10 may protrude downward from a central portion of the top plate 15. The elastic portions 21 do not necessarily extend in parallel with the central axis 1a, and the elastic portions 21 may be inclined away from the central axis 1a in the downward direction.

The four arms 20 face the puncture needle 10 to surround the puncture needle 10. Arms 20 that are adjacent to each other in the circumferential direction are separated from each other with a slit 25 therebetween. Each slit 25 extends along a plane that includes the central axis 1a, and reaches the top plate 15.

The claws 30 are provided on the bridge portions 22 that constitute leading end portions of the arms 20. The claws 30 protrude toward the puncture needle 10 from the surfaces of the bridge portions 22 that face the puncture needle 10. Each claw 30 includes a stopper plate 31 and a rib 33 that is provided on the lower surface of the stopper plate 31. The stopper plates 31 are flat plates that each have a substantially fan-like shape or a substantially triangular shape, and face the top plate 15. The stopper plates 31 are inclined so as to approach the top plate 15 in a direction toward the central axis 1a. The ribs 33 are thin plate-like protrusions that protrude downward (or toward the central axis 1a) from the lower surfaces of the stopper plates 31, and extend along a plane that includes the central axis 1a. The ribs 33 extend from the leading ends 30t of the claws 30 (or the stopper plates 31) to the bridge portions 22. As most clearly shown in FIG. 1D, the contour shape of a lower edge (which is referred to as "a slidable portion" in the present invention) 33a of each of the ribs 33 that extends along a plane that includes the central axis 1a is an arc shape.

Each arm 20 has a cantilever-like supporting structure in which a portion connected to the top plate 15 is the fixed end. The elastic portions 21 included in each arm 20 are narrow rod-like members, and can be elastically bent relatively easily. The claws 30 are provided at the free ends of the arms 20. Therefore, the arms 20 can elastically deform such that the claws 30 move away from the puncture needle 10. The arms 20 are allowed to deform due to each elastic portion 21 bending substantially along a plane that includes the central axis 1a. Since a slit 25 is provided between arms 20 that are adjacent to each other, each arm 20 can deform independent of each other.

A connector 40 is provided above the tubular portion 14. As shown in FIGS. 1C and 1D, the connector 40 includes a cylindrical portion 41 that has a substantially circular cylinder shape, a partition member (which may be referred to as "a septum") 42 that is provided on the upper end of the cylindrical portion 41, and a cap 43 that covers the partition member 42. An inner cavity 41a inside the cylindrical portion 41 communicates with the flow channel 11 inside the puncture needle 10. The partition member 42 is made of an elastic material such as rubber, and is a thin plate that has a circular shape in plan view. A slit (a cut) 42a that has a straight line shape and penetrates through the partition member 42 in the vertical direction is formed in the central portion of the partition member 42. The partition member 42 is placed on the upper end of the cylindrical portion 41, and the cap 43 is placed from above to cover the partition member 42. An engagement protrusion 41p that protrudes from the outer circumferential surface of the cylindrical portion 41 is fitted into an engagement hole 43h that penetrates through a peripheral wall of the cap 43, and thus the engagement protrusion 41p engages with the edge of the engagement hole 43h (see FIG. 1C). The partition member 42 is sandwiched between the cylindrical portion 41 and the cap 43 in the vertical direction. The slit 42a in the partition member 42 is exposed to the outside within an opening 43a that is formed in the upper surface of the cap 43 (see FIG. 1A). Upon a male Luer fitting (not shown) that has a cylindrical shape without a sharp leading end being inserted into the slit 42a of the partition member 42, the partition member 42 elastically deforms, and the male Luer fitting communicates with the inner cavity 41a in the cylindrical portion 41. Upon the male Luer fitting being pulled out of the partition member 42, the partition member 42 immediately returns to its original state, and the slit 42a closes so as to be liquid-tight. In this way, the partition member 42 serves as a self-closing type valve member. Such a self-closing type connector 40 is also referred to as "a needleless port".

A portion of the adapter 1 other than the partition member 42 and the cap 43 is preferably manufactured as one integrated part by injecting a resin material into a mold. There are no restrictions on the resin material that can be used, and polyethylene, polypropylene, polycarbonate, styrene ethylene, polyethylene terephthalate, polybutylene terephthalate, butylene styrene block copolymer, and the like can be listed as examples. However, considering cases of usage for medical purposes and that the arms 20 elastically deform, a polyolefin resin such as polyethylene or polypropylene is preferable. Although there are no restrictions on the material of the cap 43, a hard material is preferable. For example, a resin material such as polycarbonate, polypropylene, polyacetal, polyamide, rigid polyvinyl chloride, polyethylene, or the like may be used. Although there are no restrictions on the material of the partition member 42, a soft material having rubber elasticity is preferable. For example, a rubber material such as isoprene rubber, silicone rubber, or butyl rubber, or thermoplastic elastomer or the like may be used.

Next, a method for using the adapter 1 according to the present Embodiment 1 with the above-described configuration will be described. Hereinafter, a case in which the adapter 1 is connected to a vial bottle will be described as an example.

Figure 2:
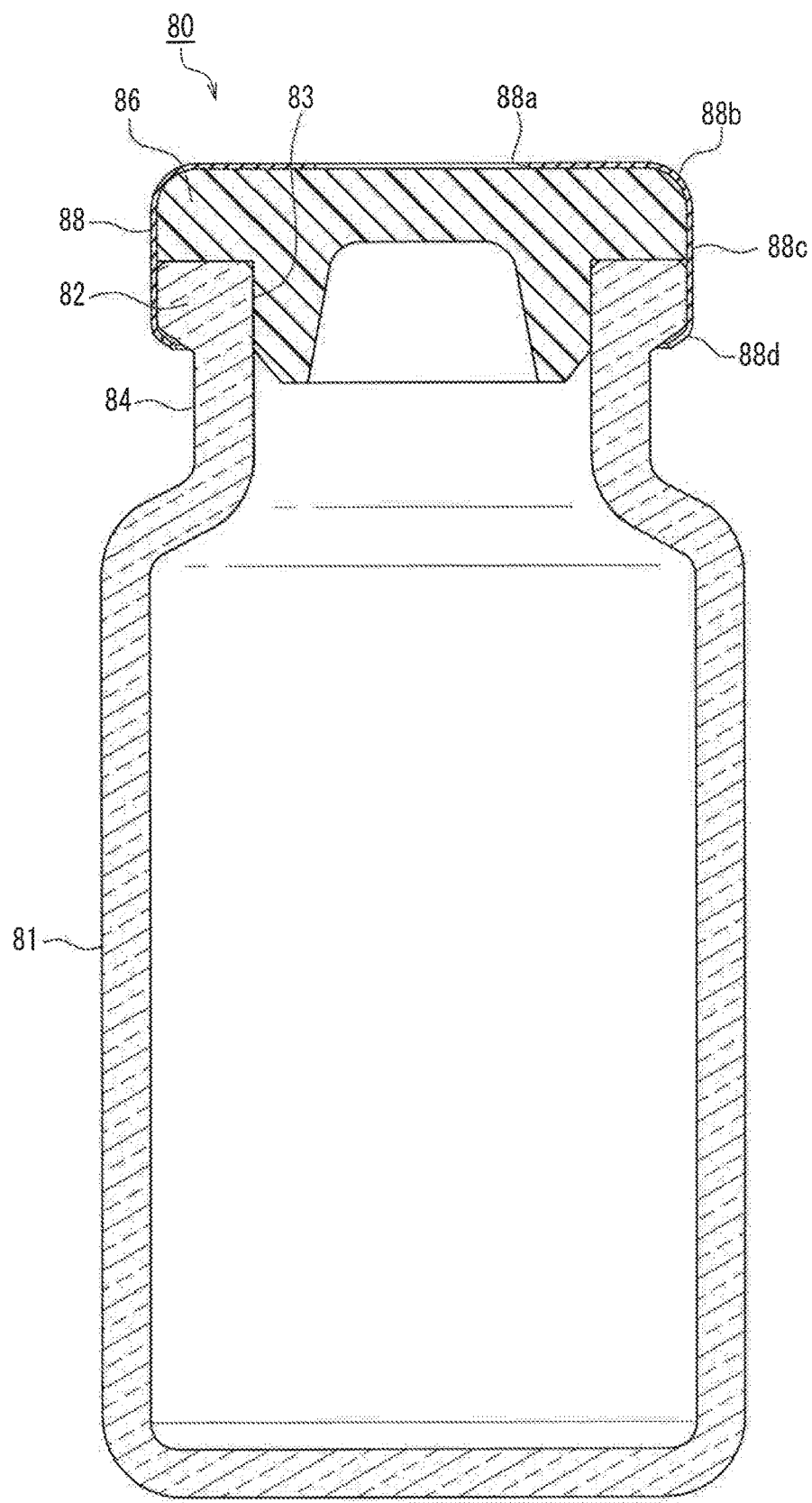
FIG. 2 is a cross-sectional view of a vial bottle to which the adapter according to the present invention is to be connected.

FIG. 2 is a cross-sectional view of an example of a vial bottle 80. The vial bottle 80 is a sealed container whose mouth (opening) 83, which is surrounded by a flange 82 that has an expanded diameter at the upper end of a bottle body 81, is sealed so as to be airtight and liquid-tight by fitting a plug member (a rubber plug) 86, which has substantially the same outer diameter as the flange 82, into the mouth 83. The outer circumferential surface of the flange 82 is a substantially circular cylindrical surface that has a larger outer diameter than a portion (a constricted portion) 84 immediately below the flange 82. Therefore, a step-like portion is formed between the flange 82 and the constricted portion 84 due to the difference between the outer diameters thereof.

To prevent the plug member 86 from falling out off the mouth 83 of the bottle body 81, a cap 88 is attached to the plug member 86 and the flange 82. The cap 88 is a sheet of metal (e.g. aluminum), resin, or the like, and is intimately attached to the plug member 86 and the flange 82. The lower end of the cap 88 reaches a position that is downward of the outer circumferential surface of the flange 82, which has a substantially circular cylindrical surface. The upper end of the cap 88 reaches the upper surface of the plug member 86. A central area of the upper surface of the plug member 86 is exposed to the outside from an opening 88a that is circular and is provided in the cap 88 (see FIG. 3 described below).

The outer circumferential surface of the plug member 86 and the outer circumferential surface of the flange 82 are circular cylindrical surfaces that have substantially the same diameter. Therefore, an outer circumferential surface 88c of the cap 88 attached to the plug member 86 and the flange 82 is also a substantially circular cylindrical surface. The upper end of the outer circumferential surface 88c of the cap 88 (or the outer peripheral edge of the upper surface of the cap 88) is referred to as an upper edge 88b, and the lower end of the outer circumferential surface 88c is referred to as a lower edge 88d.

The vial bottle 80 is not necessarily provided with the cap 88. In such a case, the upper edge 88b, the lower edge 88d, and the outer circumferential surface 88c mean the positions corresponding to the plug member 86 or the flange 82.

A powdered drug (not shown) is enclosed in the vial bottle 80.

Figure 3:
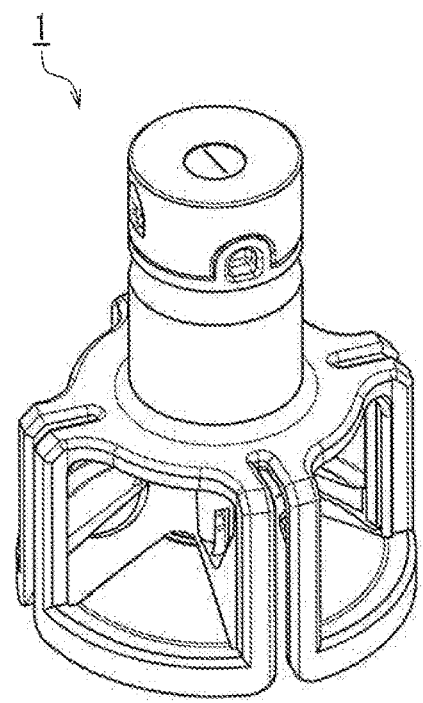
FIG. 3 is a perspective view showing a state of the adapter according to Embodiment 1 of the present invention before being connected to a vial bottle.
Figure 3:
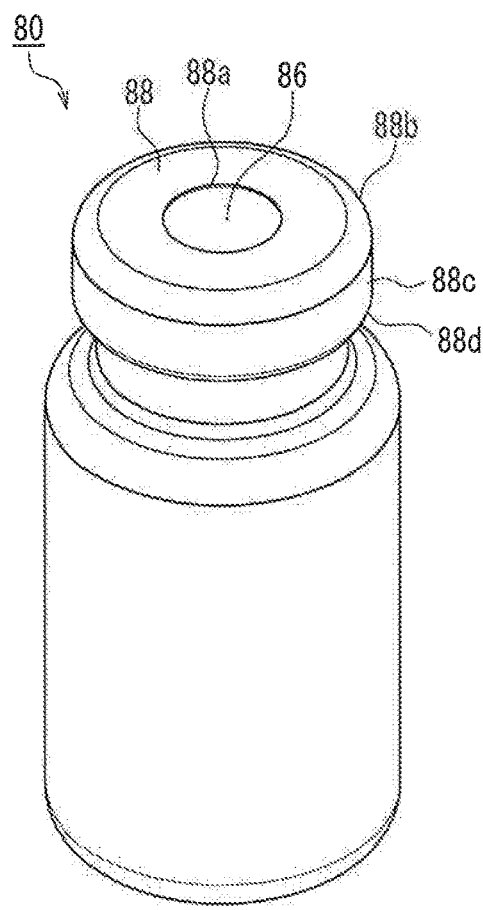

First, as shown in FIG. 3, the adapter 1 is orientated to face the plug member (the female connector) 86 of the vial bottle 80. From this state, the adapter 1 is brought closer to the plug member 86.

Figure 4:
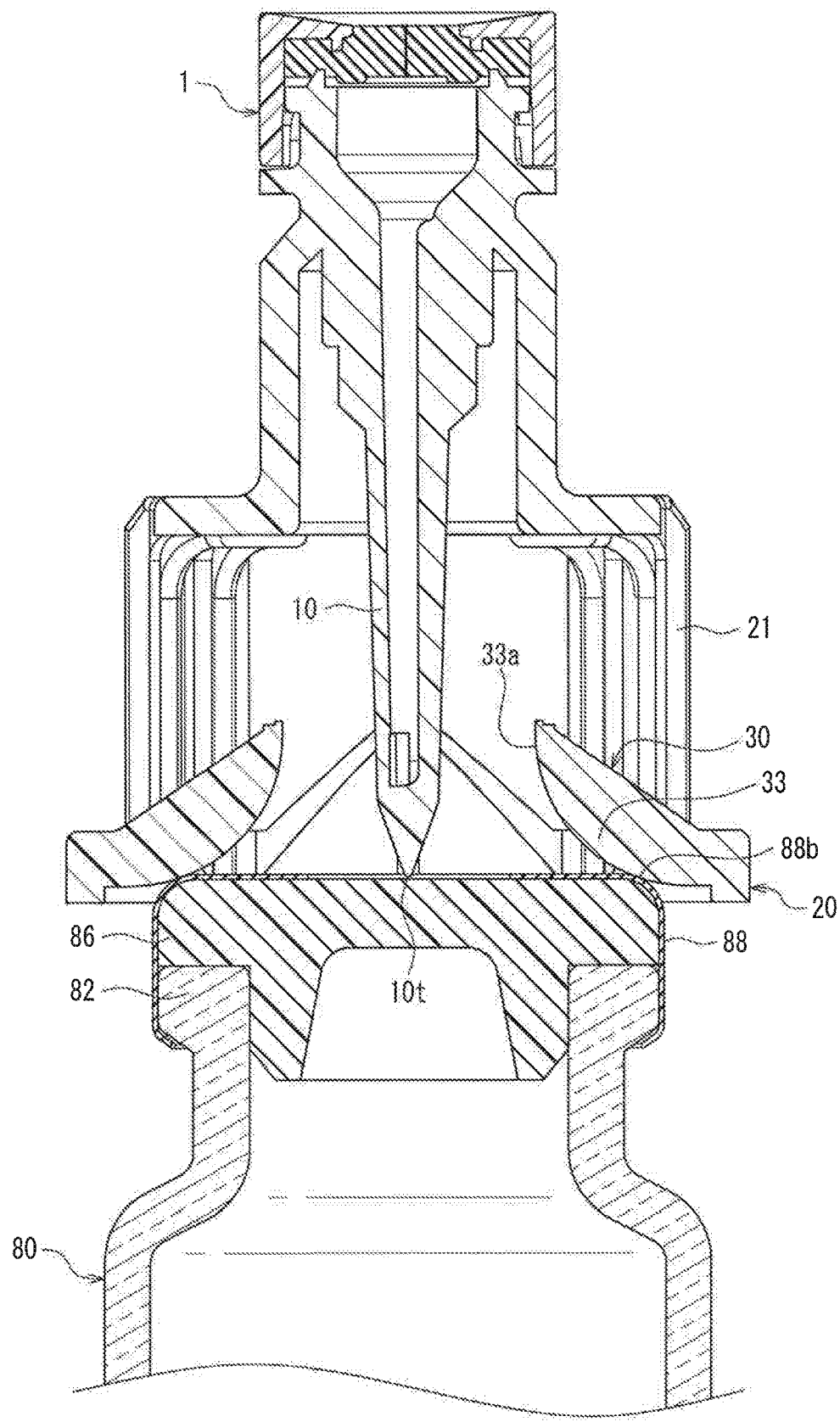
FIG. 4 is a cross-sectional view showing a first state of the adapter according to Embodiment 1 of the present invention in the course of being connected to a vial bottle.

The inner diameter of the adapter 1 at the leading ends 33t of the claws 30 is smaller than the outer diameter of the cap 88 of the vial bottle 80. Therefore, as shown in FIG. 4, the leading end 10t of the puncture needle 10 abuts against the plug member 86 that is exposed to the outside within the opening 88a of the cap 88, and almost at the same time, or in tandem with that, the slidable portions 33a of the ribs 33 of the claws 30 abut against the upper edge 88b of the cap 88.

Figure 5:
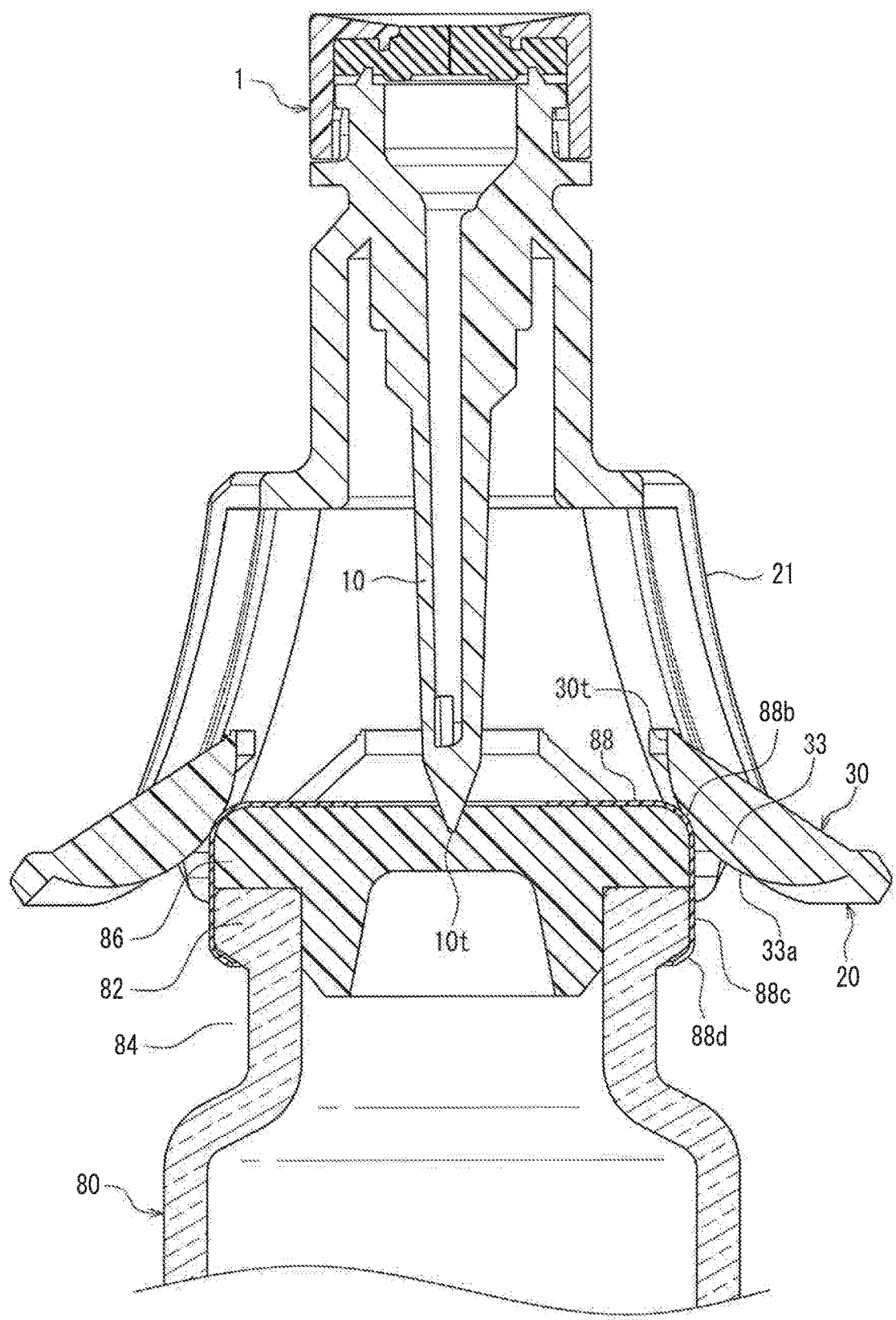
FIG. 5 is a cross-sectional view showing a second state of the adapter according to Embodiment 1 of the present invention in the course of being connected to a vial bottle.

Upon the adapter 1 being pressed toward the vial bottle 80, the puncture needle 10 is inserted into the plug member 86 as shown in FIG. 5, and simultaneously, the slidable portions 33a of the claws 30 slide on the upper edge 88a of the cap 88. While sliding on the upper edge 88a, the slidable portions 33a move the claws 30 away (outward) from the puncture needle 10 in radial directions. The claws 30 are able to move due to the elastic portions 21 of the arms 20 elastically bending. Thereafter, the leading ends 30t of the claws 30 move past the upper edge 88b, and then slide downward on the outer circumferential surface 88c of the cap 88. Upon the leading ends 30t reaching the lower edge 88d of the cap 88, the elastic portions 21 elastically recover, and the claws 30 are fitted into the constricted portion 84 below the flange 82.

Figure 6:
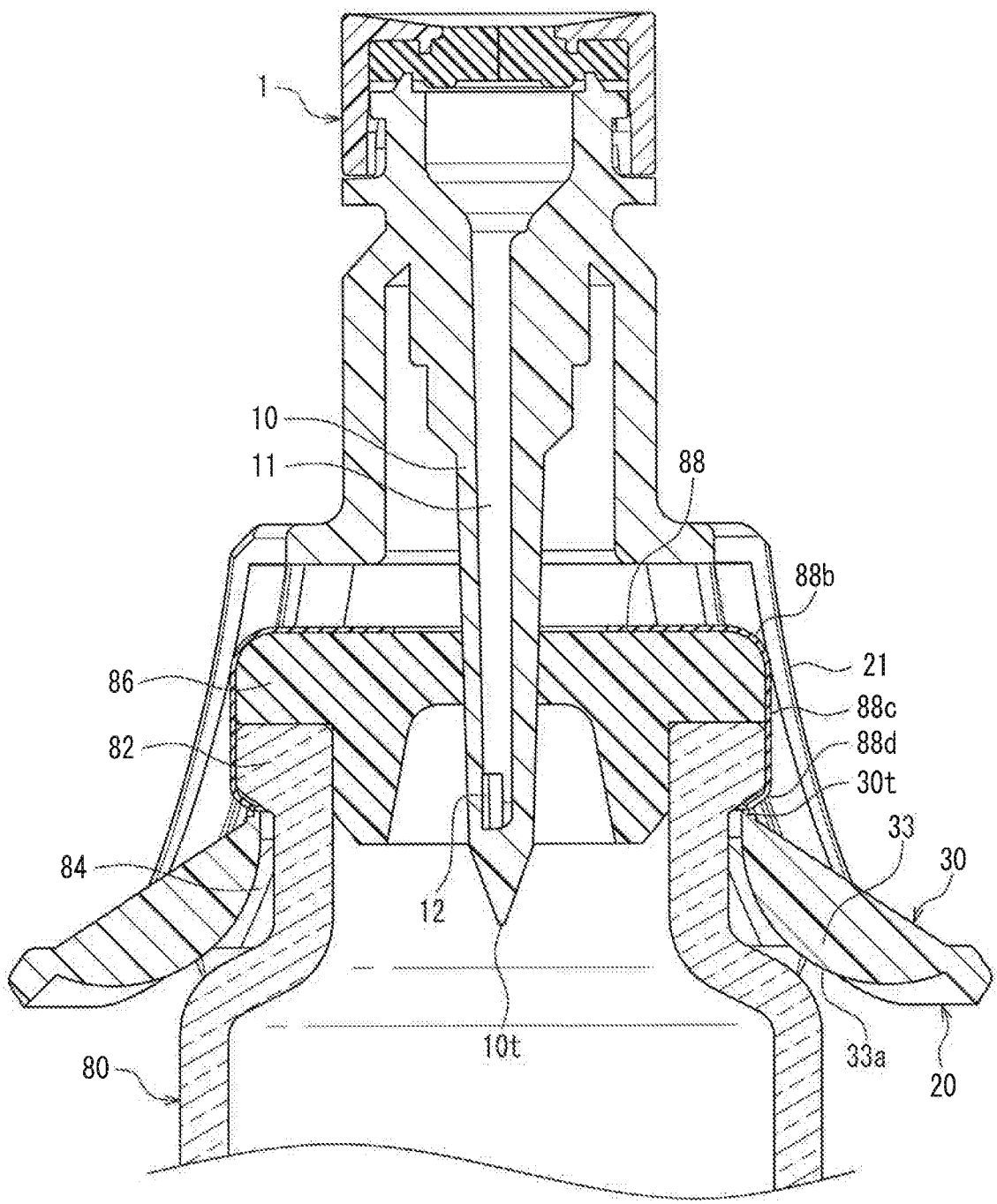
FIG. 6 is a cross-sectional view showing a state of the adapter according to Embodiment 1 of the present invention connected to a vial bottle.

Thus, as shown in FIG. 6, the adapter 1 can be connected to the vial bottle 80.

The puncture needle 10 penetrates through the plug member 86, and the opening 12, which is formed near the leading end of the puncture needle 10, is exposed, below the plug member 86. Therefore, the flow channel 11 in the puncture needle 10 communicates with the inner cavity of the vial bottle 80.

The claws 30 engage with the flange 82, which has an expanded diameter. Therefore, even if a pulling force or vibrations are applied to the adapter 1 and the vial bottle 80 in a direction in which the adapter 1 and the vial bottle 80 are separated from each other, the puncture needle 10 does not unintentionally come out of the plug member 86.

Figure 12:
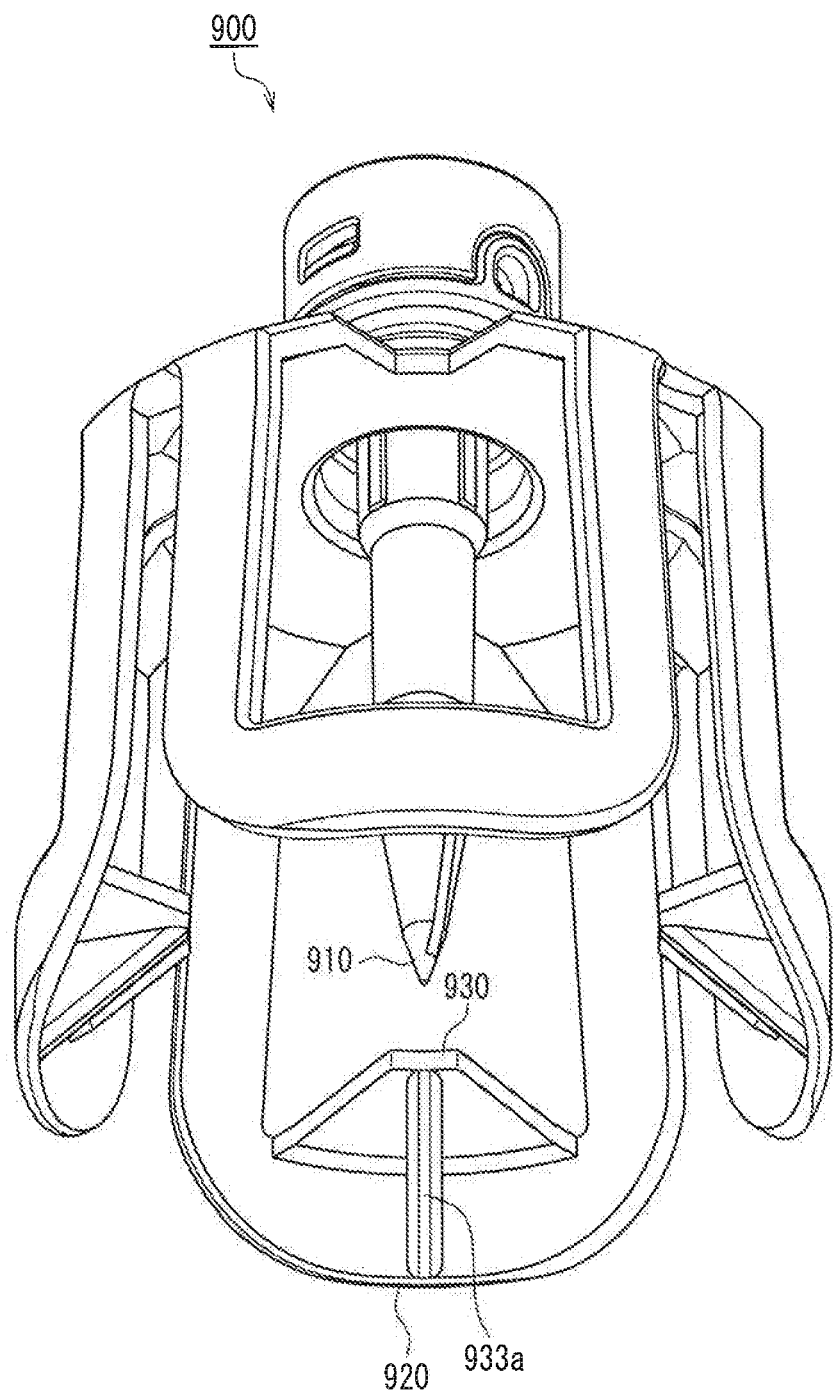
FIG. 12 is a perspective view of a conventional adapter seen from below.

Compared to the conventional adapter 900 (see FIG. 12) in which the contour shape of each of the slidable portions 933a of the claws 930 is a straight line shape, the adapter 1 according to the present Embodiment 1 is significantly different in that the contour shape of each of the slidable portions 33a of the claws 30 is an arc shape when seen in a direction that is orthogonal to the central axis 1a as shown in FIG. 1D. Due to such differences, the adapter 1 according to the present invention requires a smaller force when being connected to the vial bottle 80, compared to the conventional adapter 900. The following describes reasons therefor.

Figure 7A:
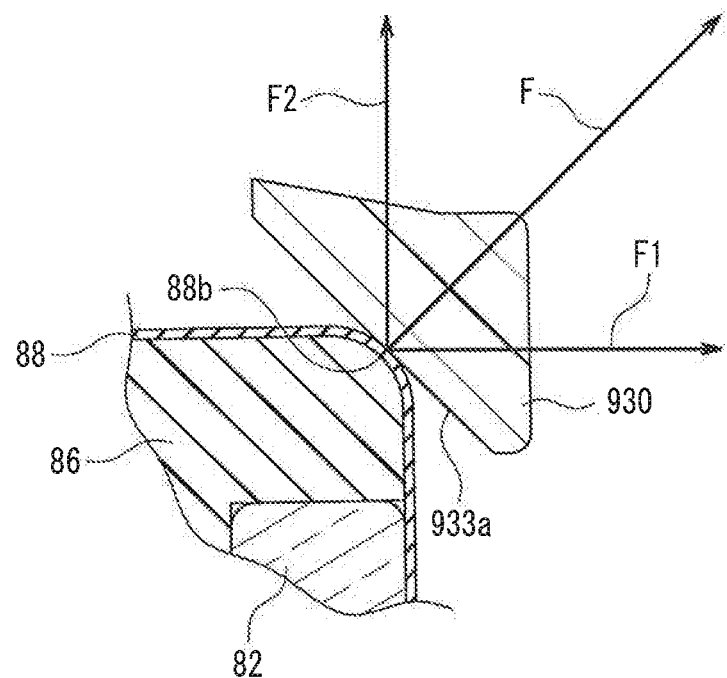
FIGS. 7A and 7B are cross-sectional views showing a reactive force that is applied to claws during a process in which a conventional adapter is connected to a vial bottle.

FIG. 7A is a cross-sectional view showing a state in which a claw 930 of the conventional adapter 900 abuts against the upper edge 88b of the cap 88 of the vial bottle 80 for the first time (a state corresponding to FIG. 4 for the present Embodiment 1). The cross section in FIG. 7A includes a central axis that passes through the puncture needle 910 and a slidable portion 933a of a claw 930. For the sake of simplification, FIG. 7A shows only one claw 930 that is included in the adapter 900.

In this state, a downward force is applied to the adapter 900 toward the vial bottle 80. At this time, the claw 930 receives a reactive force F from the upper edge 88b of the cap 88. The direction of the reactive force F is orthogonal to the tangent line at the contact point between the slidable portion 933a and the upper edge 88b. Since the contour shape of the slidable portion 933a is a straight line shape, the direction of the reactive force F is orthogonal to the slidable portion 933a. Since the slidable portion 933a is inclined relative to the vertical direction, the direction of the reactive force F is also inclined relative to the vertical direction. The reactive force F can be divided into a horizontal direction component F1 and a vertical direction component F2. The horizontal direction component F1 contributes to the elastic bending of the arm 920.

Figure 7B:
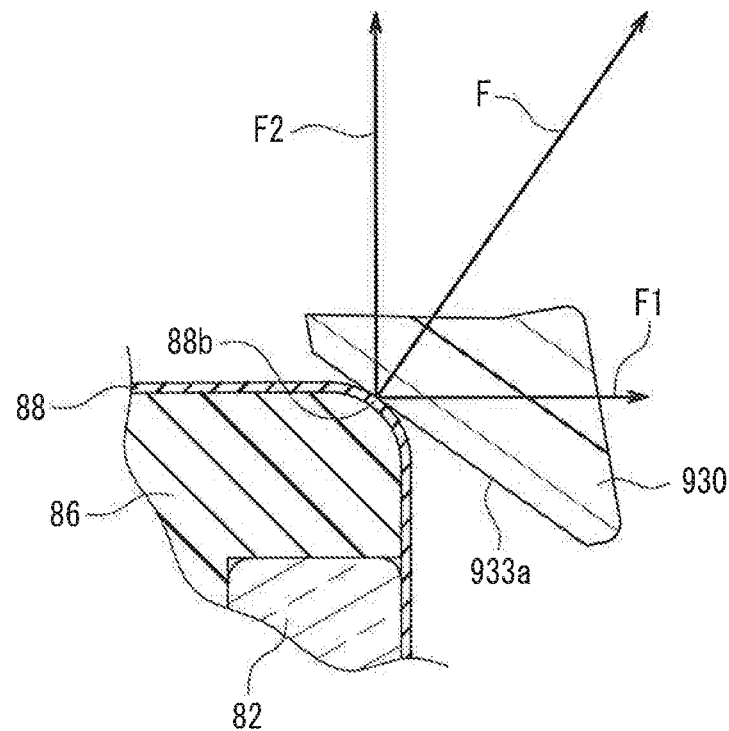

As the adapter 900 is pressed toward the vial bottle 80, the arm 920 elastically deforms, and the claw 930 moves outward in a radial direction while sliding on the upper edge 88b. The attitude (the inclination) of the claw 930 changes while it moves in the radial direction. FIG. 7B is a cross-sectional view showing a state in which the claw 930 has moved outward in the radial direction (a state corresponding to FIG. 5 for the present Embodiment 1). Compared to FIG. 7A, the inclination of the slidable portion 933a relative to the horizontal direction is smaller. Thus, the direction of the reactive force F that the claw 930 receives from the upper edge 88b is changed to be closer to the vertical direction. To facilitate understanding, the length of the arrow that indicates the reactive force F in FIG. 7B is matched with that of the reactive force F in FIG. 7A. In FIG. 7B, compared to FIG. 7A, the horizontal direction component F1 of the reactive force F is smaller, and the vertical direction component F2 of the reactive force F is greater. That is, the ratio of the horizontal direction component F1 to the vertical direction component F2, i.e. F1/F2, is smaller. This means that the efficiency of conversion from a downward force that is applied to the adapter 900 to the horizontal direction component F1 that contributes to the elastic bending of the arm 920 is lower. Therefore, in the state shown in FIG. 7B, compared to the state shown in FIG. 7A, it is necessary to apply a greater downward force to the adapter 900 to move the claw 930 further outward in the radial direction. In this way, as the claw 930 moves further outward, a greater force needs to be applied to the adapter 900 to move the claw 930 even further outward. Therefore, it gradually becomes difficult to move the claw 930 outward. Also, since the reactive force F increases as the force applied to the adapter 900 increases, a friction force between the slidable portion 933a and the upper edge 88b increases. This force makes it even more difficult to move the claw 930 outward.

Also, in the case of connecting the adapter 900 to a vial bottle 80 that has a cap 88 with a larger outer diameter, it is necessary to move the claw 930 outward by a longer distance. Therefore, the ratio F1/F2 is even smaller, and it is necessary to apply an even greater force to the adapter 900. Therefore, it is practically difficult to connect the adapter 900 to a vial bottle 80 that has a cap 88 with a large outer diameter, and the size range of vial bottles 80 to which the adapter 900 can be connected is small.

Figure 8A:
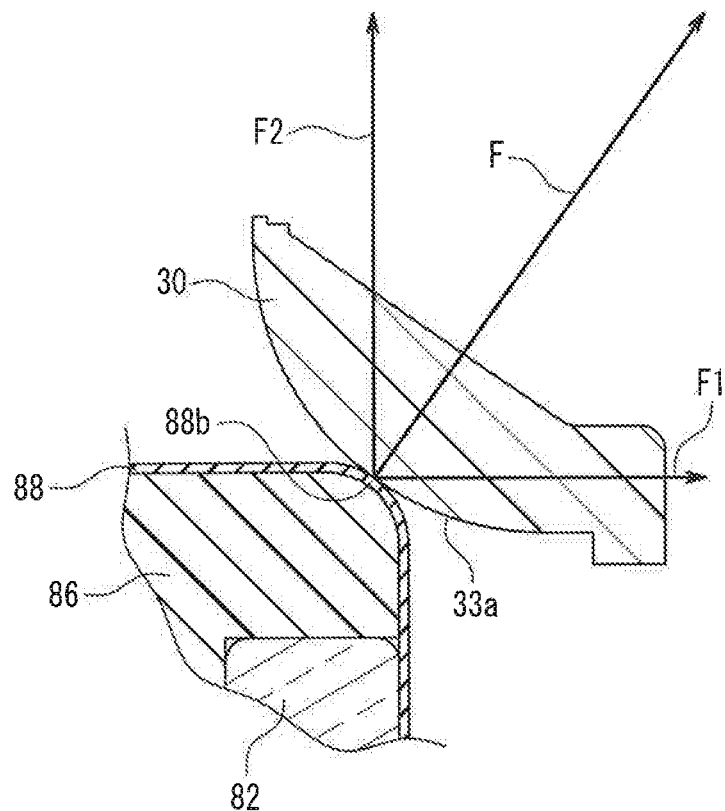
FIGS. 8A and 8B are cross-sectional views showing a reactive force that is applied to claws during a process in which the adapter according to Embodiment 1 of the present invention is connected to a vial bottle.
Figure 8B:
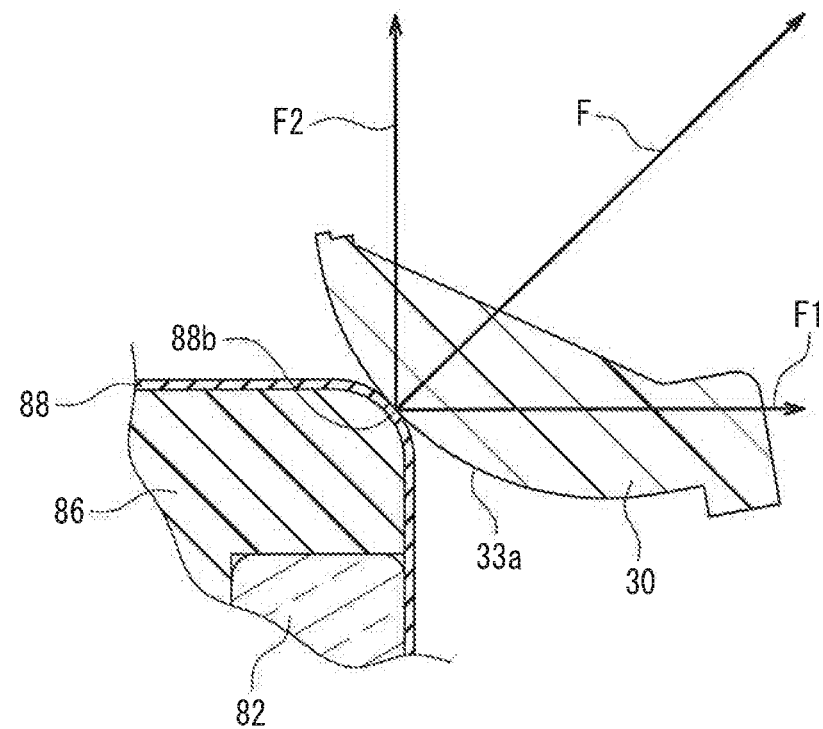

FIGS. 8A and 8B are cross-sectional views showing the reactive force F that a claw 30 receives from the cap 88 in the adapter 1 according to the present Embodiment 1, in the same manner as in FIGS. 7A and 7B. FIG. 8A is a cross-sectional view showing a state in which a claw 30 abuts against the upper edge 88b of the cap 88 of the vial bottle 80 for the first time (the state shown in FIG. 4). As in FIG. 7A, the claw 30 receives the reactive force F from the upper edge 88b. The reactive force F can be divided into a horizontal direction component F1 and a vertical direction component F2. FIG. 8B is a cross-sectional view showing a state in which the claw 30 has moved outward in a radial direction (the state shown in FIG. 5) as a result of the adapter 1 being pressed toward the vial bottle 80. There is a change in the attitude (the inclination) of the claw 30. Also, the direction of the reactive force F is changed to be closer to the horizontal direction. In FIG. 8B, compared to FIG. 8A, the horizontal direction component F1 of the reactive force F is greater, and the vertical direction component F2 of the reactive force F is smaller. Conversely to the change in the ratio F1/F2 from the FIG. 7A to FIG. 7B for the conventional adapter 900, the ratio F1/F2 increases in the present Embodiment 1. Therefore, in the present Embodiment 1, the force that is to be applied to the adapter 1 is allowed to decrease as the claw 30 moves outward while sliding on the upper edge 88b of the cap 88. Furthermore, the friction force between the slidable portions 33a and the upper edge 88b accordingly decreases. This is an advantage in terms of further reduction of the force that is to be applied to the adapter 1.

Also, in the case of connecting the adapter 1 to a vial bottle 80 that has a cap 88 with a larger outer diameter, it is necessary to move the claw 30 outward by a longer distance. Therefore, the ratio F1/F2 is even greater than that in FIG. 8B, and the force that is to be applied to the adapter 1 can be even smaller. Therefore, compared to the conventional adapter 900, the adapter 1 according to the present Embodiment 1 can be connected to a vial bottle 80 that has a cap 88 with a larger outer diameter. Therefore, the size range of vial bottles 80 that can be connected is large. Actually, vial bottles with various sizes are available on the market. It is unnecessary to prepare a plurality of types of adapter 1 according to the present Embodiment 1 for vial bottles with different sizes.

As described above, the contour shape of each of the slidable portions 33a of the claws 30 according to the present invention is significantly different from that of each of the slidable portions 933a of the conventional adapter 900. Therefore, with the present invention, the horizontal direction component F1 can be stably generated from a downward force that is applied to the adapter 1, regardless of the positions of the claws 30 in radial directions. Also, the vertical direction component F2, which acts against a downward force that is applied to the adapter 1, does not become excessive. As a result, it is possible to connect the adapter 1 to a vial bottle 80 without applying a large downward force to the adapter 1.

In the above-described Embodiment 1, the ratio F1/F2 increases as the claws 30 move outward. However, the present invention is not limited in this way. The ratio F1/F2 may decrease as the claws 30 move outward, or may be substantially constant. Preferably, the ratio F1/F2 is substantially constant or increases.

Changes in the ratio F1/F2 during a process in which the slidable portions 33a slide on the upper edge 88b while the claws 30 move outward vary depending on the contour shape of each slidable portion 33a. In the present Embodiment 1, the contour shape of each slidable portion 33a is an arc shape. However, the present invention is not limited in this way. Generally, if the contour shape of each slidable portion 33a includes a smooth convex curve, the ratio F1/F2 can be kept high, and the force that is to be applied to the adapter 1 so as to be connected to a vial bottle 80 can be small. For example, the contour shape of each slidable portion 33a may be the shape of a portion of an ellipse, or the shape of any convex curve in which the curvature changes depending on the position in a radial direction. It is preferable that the contour shape of each slidable portion 33a is constituted by only smooth convex curves. However, the contour shape of each slidable portion 33a may be constituted by a combination of a convex curve and a straight line that are smoothly connected to each other. If a convex curve and a straight line are combined, it is preferable that the straight line is located outward of the convex curve in a radial direction. It is unfavorable that the contour shape of each slidable portion 33a includes a concave curve. This is because a concave curve may sharply reduce the ratio F1/F2. The contour shape of each slidable portion 33a is appropriately designed to avoid a situation in which it is necessary to apply an excessive force to the adapter 1 to connect the adapter 1 to a vial bottle 80.

Preferably, the above-described "smooth convex curve" provided in each slidable portion 33a is a curve of which the angle of inclination relative to the horizontal direction (i.e. the tangent line of each slidable portion 33a) increases in a direction toward the central axis 1a in the initial state in which the arms 20 are not deformed (see FIG. 1D). As a result, the innermost ends of the slidable portions 33a (the positions that are closest to the central axis 1a) are located at the highest positions (the uppermost positions) of the slidable portions 33a. The leading ends 30t of the claws 30 are located at the uppermost positions of the slidable portions 33a.

To reduce a friction force that is generated when the slidable portions 33a of the claws 30 slide on the upper edge 88b of the cap 88, it is preferable that the contact areas of the slidable portions 33a and the upper edge 88b are small. Providing slidable portions 33a on the thin plate-like ribs 33 that extend along a plane that includes the central axis 1a as in the above-described Embodiment 1 results in a reduction in the contact areas of the slidable portions 33a and the cap 88 and a reduction in the friction force therebetween, and therefore such a configuration is advantageous in that the force that is to be applied to the adapter 1 can be further reduced.

The above-described Embodiment 1 is merely an example. The present invention is not limited to the above-described Embodiment 1, and may be modified as appropriate. In particular, configurations other than the slidable portions 33a of the claws 30 can be modified in any manner.

For example, the shape of the arms 20 for which the claws 30 are provided may be modified in any manner. It is not essential that the arms have a substantially "U" like shape. Also, it is not essential that the openings 23 that are each surrounded by an arm and the top plate 15 are formed. Each arm may have, for example, a strip shape (a substantially "I" like shape) that extends downward from the outer peripheral edge of the top plate 15 so as to face the puncture needle 10.

The number of arms is not limited to four, and may be greater or smaller than 4. However, it is preferable that the number of arms is two or more, and the arms are equiangularly located with respect to the central axis 1a.

The number of claws provided for one arm is not limited to one, and may be two or more.

The inclination of the stopper plates 31 of the claws 30 may be determined as desired. It is not essential that the stopper plates 31 are inclined relative to the horizontal direction, and may be parallel with the horizontal direction, for example. The stopper plates 31 may be omitted, and the claws may be constituted by only the ribs 33 (i.e. plate-like objects that each extend along a plane that includes the central axis 1a).

Embodiment 2

The following describes an adapter 2 according to Embodiment 2 of the present invention, mainly focusing on differences from the adapter 1 according to Embodiment 1. In the drawings showing the adapter 2, referenced in the following description, members that are identical with the members that constitute the adapter 1 according to Embodiment 1 are denoted by identical reference signs, and descriptions thereof are omitted.

Figure 9A:
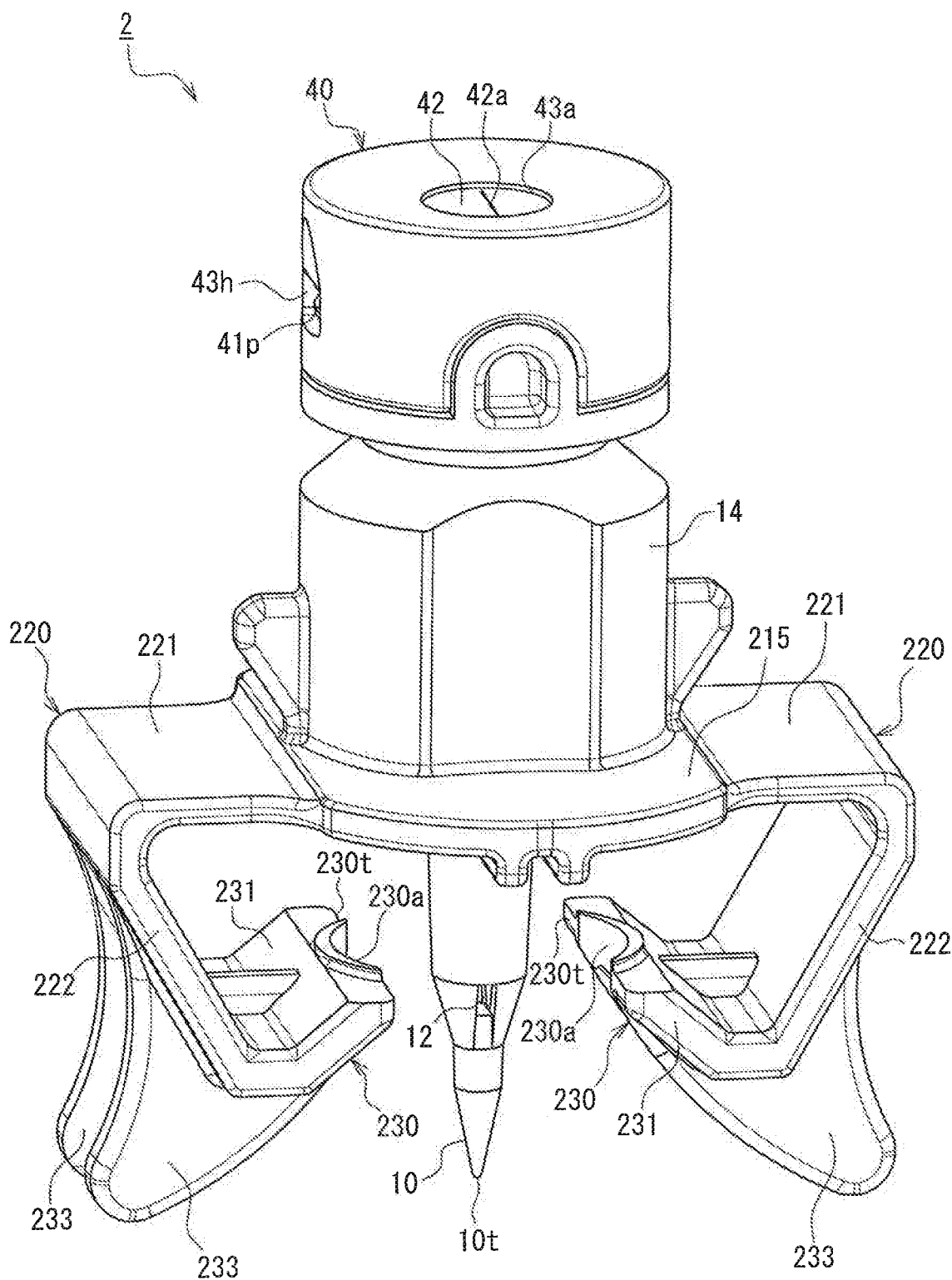
FIG. 9A is a perspective view showing an adapter according to Embodiment 2 of the present invention seen from above.
Figure 9B:
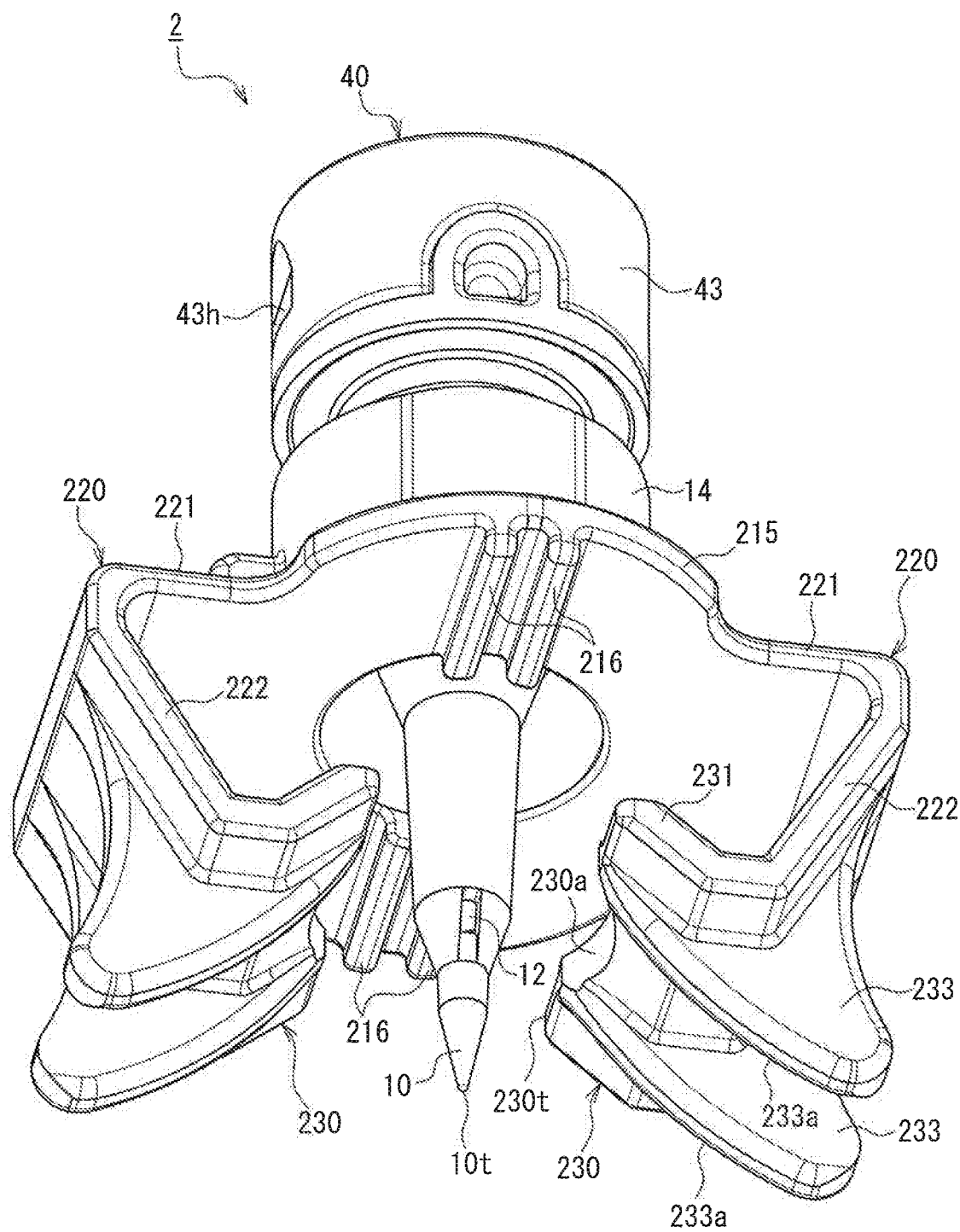
FIG. 9B is a perspective view showing the adapter according to Embodiment 2 of the present invention seen from below.
Figure 9C:
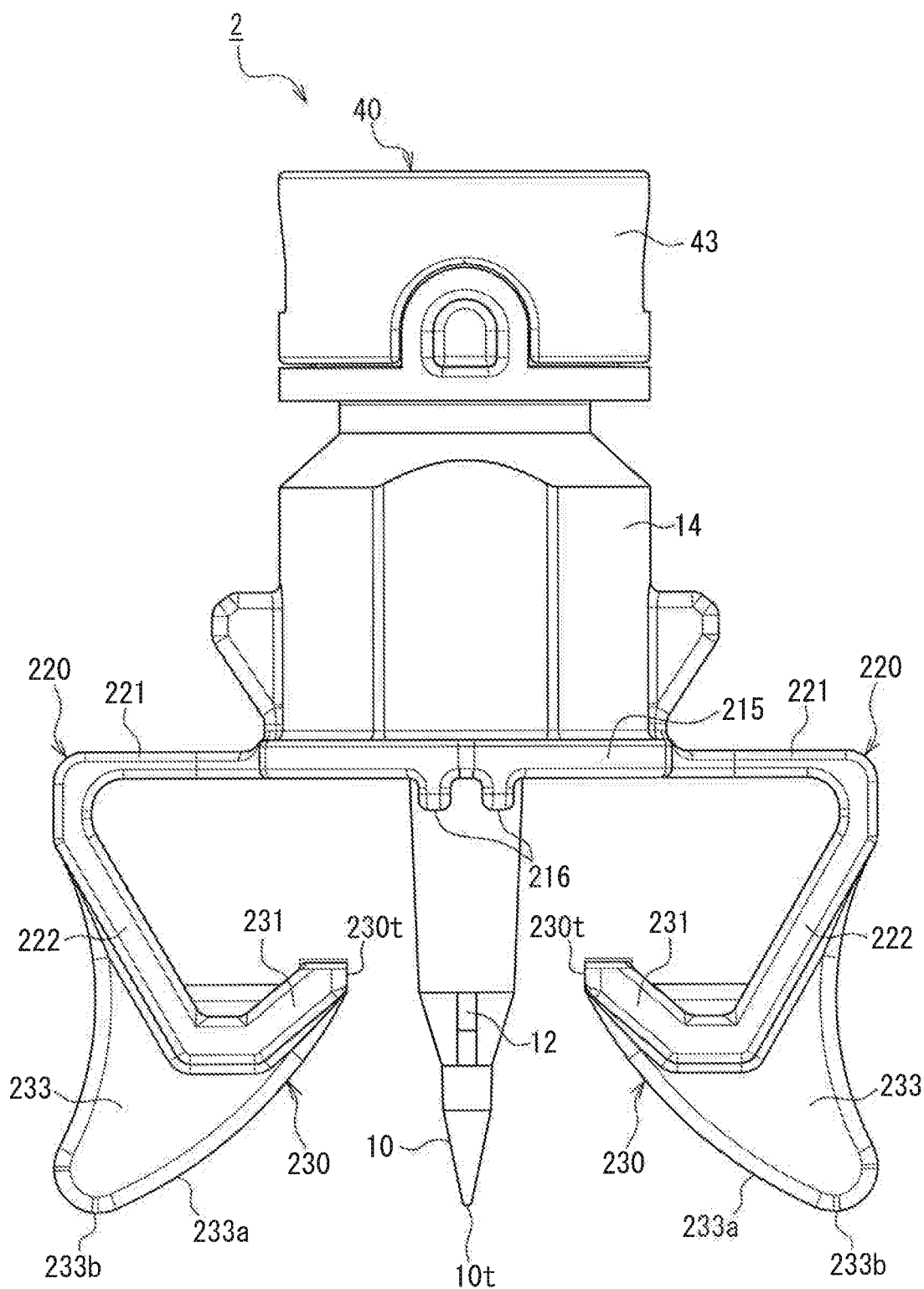
FIG. 9C is a side view showing the adapter according to Embodiment 2 of the present invention.
Figure 9D:
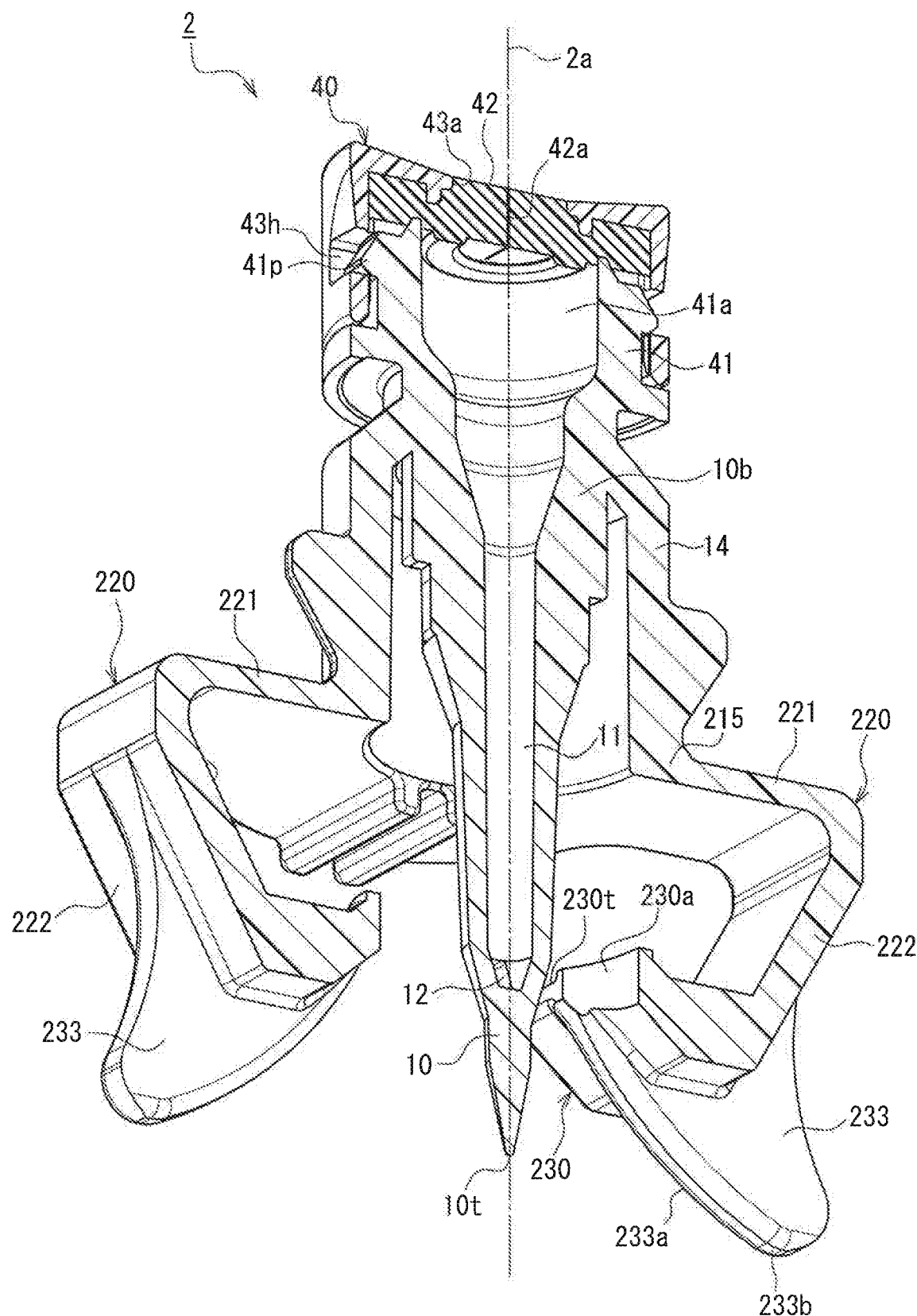
FIG. 9D is a cross-sectional perspective view showing the adapter according to Embodiment 2 of the present invention seen from below.

FIG. 9A is a perspective view showing the adapter 2 according to Embodiment 2 of the present invention seen from above. FIG. 9B is a perspective view of the adapter 2 seen from below, FIG. 9C is a side view of the adapter 2, and FIG. 9D is a cross-sectional perspective view of the adapter 2 seen from below. In FIG. 9D, a two-dot chain line 2a is the central axis of the adapter 2.

As shown in FIG. 9D, the upper end of the tubular portion 14 is connected to the base end portion 10b of the puncture needle 10. A top plate 215 is provided on the lower end of the tubular portion 14. As can be understood from FIG. 9A, the top plate 215 is a thin plate that extends in the horizontal direction. The top plate 215 has a substantially the same shape as the shape of an athletic track in plan view from above. Two arms 220 are respectively provided on two sides of the top plate 215 that face each other in the minor axis direction of the top plate 215.

Each arm 220 includes a shoulder portion 221 that extends substantially in parallel with a radial direction, and a suspended portion 222 that extends downward from the distal end of the shoulder portion 221 (an end portion that is furthest from the puncture needle 10). The suspended portions 222 face the puncture needle 10. As shown in FIG. 9C, the suspended portions 222 are each inclined so as to approach the puncture needle 10 in a direction toward the lower end (i.e. the leading end) thereof.

Claws 230 are respectively provided at the leading ends of the suspended portions 222 so as to protrude toward the puncture needle 10. Each claw 230 includes a stopper plate 231 and two ribs 233 that are provided on the lower surface of the stopper plate 231. The stopper plates 231 are plate-like objects that extend from the leading ends of the suspended portions 222, and that are inclined so as to approach the top plate 215 in a direction toward a central axis 2a (or the puncture needle 10). Leading ends 230t of the claws 230 (or the stopper plates 231) are provided with recessed portions 230a that each have an arc shape that is coaxial with the puncture needle 10 (see FIG. 9A). The ribs 233 are thin plate-like protrusions that protrude downward from the lower surfaces of the stopper plates 231. The ribs 233 are not only provided on the stopper plates 231, but also extend to the outer surfaces of the suspended portions 222. Each rib 233 is parallel with a plane that includes the central axis 2a. Two ribs 233 on the same claw 230 are separated from each other, and face each other in parallel with each other. As most clearly shown in FIG. 9C, the ribs 233 have a substantially wedge-like shape. The contour shape of an edge (referred to as "a slidable portion" in the present invention) 233a of each rib 233 that faces downward (toward the puncture needle 10) is an arc shape. The slidable portions 233a that each have an arc shape extend from the leading ends 230t of the claws 230 to lower ends (i.e. the leading ends of the substantially wedge-like shapes) 233b of the ribs 233.

Each arm 220 has a cantilever-like supporting structure in which a portion connected to the top plate 215 is the fixed end. The shoulder portion 221 included in each arm 220 is a thin plate-like member and can be elastically bent relatively easily. The claws 230 are provided at the free ends of the arms 220. Therefore, the arms 220 can elastically deform such that the claws 230 move away from the puncture needle 10. The arms 220 are allowed to deform due to each shoulder portion 221 bending along a plane that includes the central axis 2a. In the present Embodiment 2, the suspended portions 222 and the stopper plates 231 are substantially not deformable because the ribs 233 are provided. However, the present invention is not limited to such a configuration. For example, the ribs 233 may only be provided on the stopper plates 231, and the suspended portions 222 may also be configured to be elastically bendable.

As shown in FIG. 9B, protrusions 216 protrude downward from the lower surface of the top plate 215. The protrusions 216 extend in the major axis direction of the top plate 215.

The connector 40 is provided above the tubular portion 14 as in Embodiment 1.

The adapter 2 according to the present Embodiment 2 can be connected to the vial bottle 80 (see FIG. 2) as with Embodiment 1.

Figure 10:
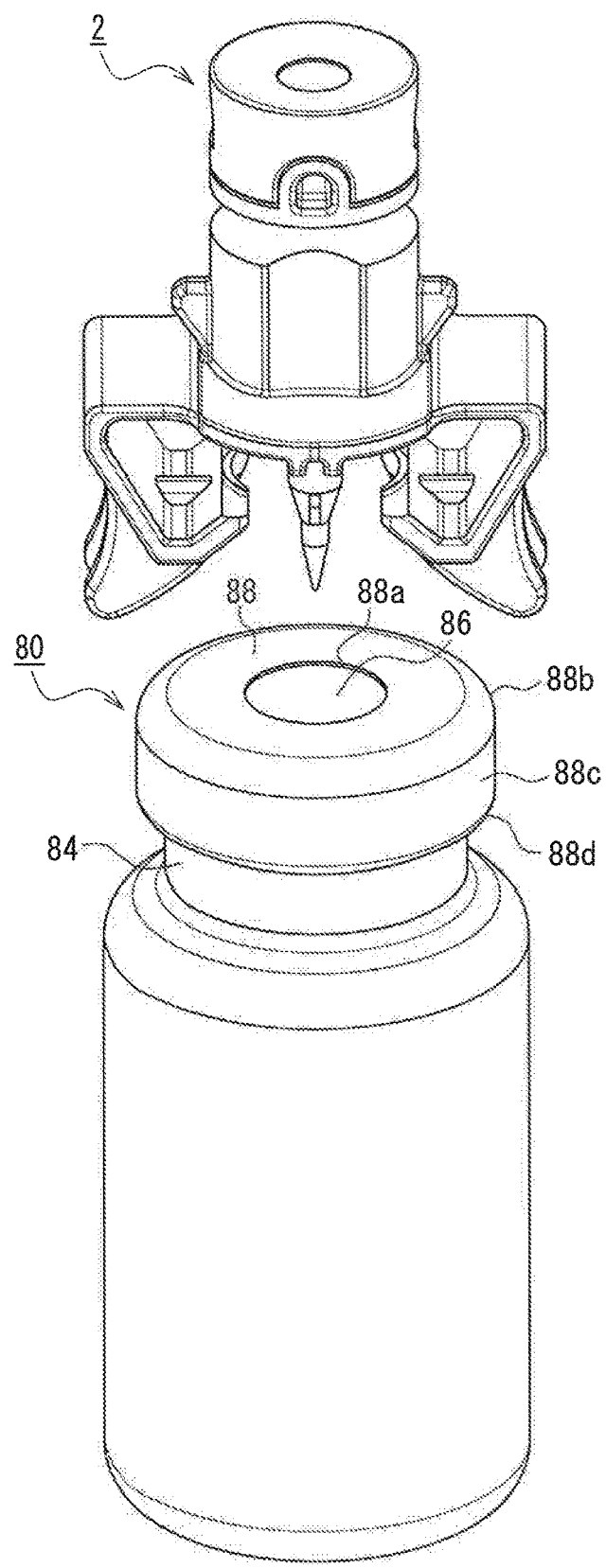
FIG. 10 is a perspective view showing a state of the adapter according to Embodiment 2 of the present invention before being connected to a vial bottle.

First, as shown in FIG. 10, the adapter 2 is orientated to face the plug member (the female connector) 86 of the vial bottle 80. From this state, the adapter 2 is brought closer to the plug member 86.

The inner diameter of the adapter 2 at the leading ends 233t of the claws 230 is smaller than the outer diameter of the cap 88 of the vial bottle 80. Therefore, the leading end 10t of the puncture needle 10 abuts against the plug member 86 that is exposed to the outside within the opening 88a of the cap 88, and almost at the same time, or in tandem with that, the slidable portions 233a of the ribs 233 of the claws 230 abut against the upper edge 88b of the cap 88.

Upon the adapter 2 being pressed toward the vial bottle 80, the puncture needle 10 is inserted into the plug member 86, and simultaneously, the slidable portions 233a of the claws 230 slide on the upper edge 88a of the cap 88. In the present Embodiment 2, two ribs 233 are provided separate from each other on each of the two arms 220. Therefore, four slidable portions 233a provided on four ribs 233 simultaneously slide on the upper edge 88a of the cap 88. Thus, it is possible to press the adapter 2 against the vial bottle 80 without allowing the adapter 2 to be inclined relative to the vial bottle 80.

While sliding on the upper edge 88a, the slidable portions 233a move the claws 230 away (outward) from the puncture needle 10 in radial directions. The claws 230 are allowed to move due to the shoulder portions 221 of the arms 220 elastically bending.

Thereafter, the leading ends 230t of the claws 230 move past the upper edge 88b, and then slide downward on the outer circumferential surface 88c of the cap 88. Upon the leading ends 230t reaching the lower edge 88d of the cap 88, the shoulder portions 221 elastically recover, and the claws 230 are fitted into the constricted portion 84 below the flange 82.

Figure 11A:
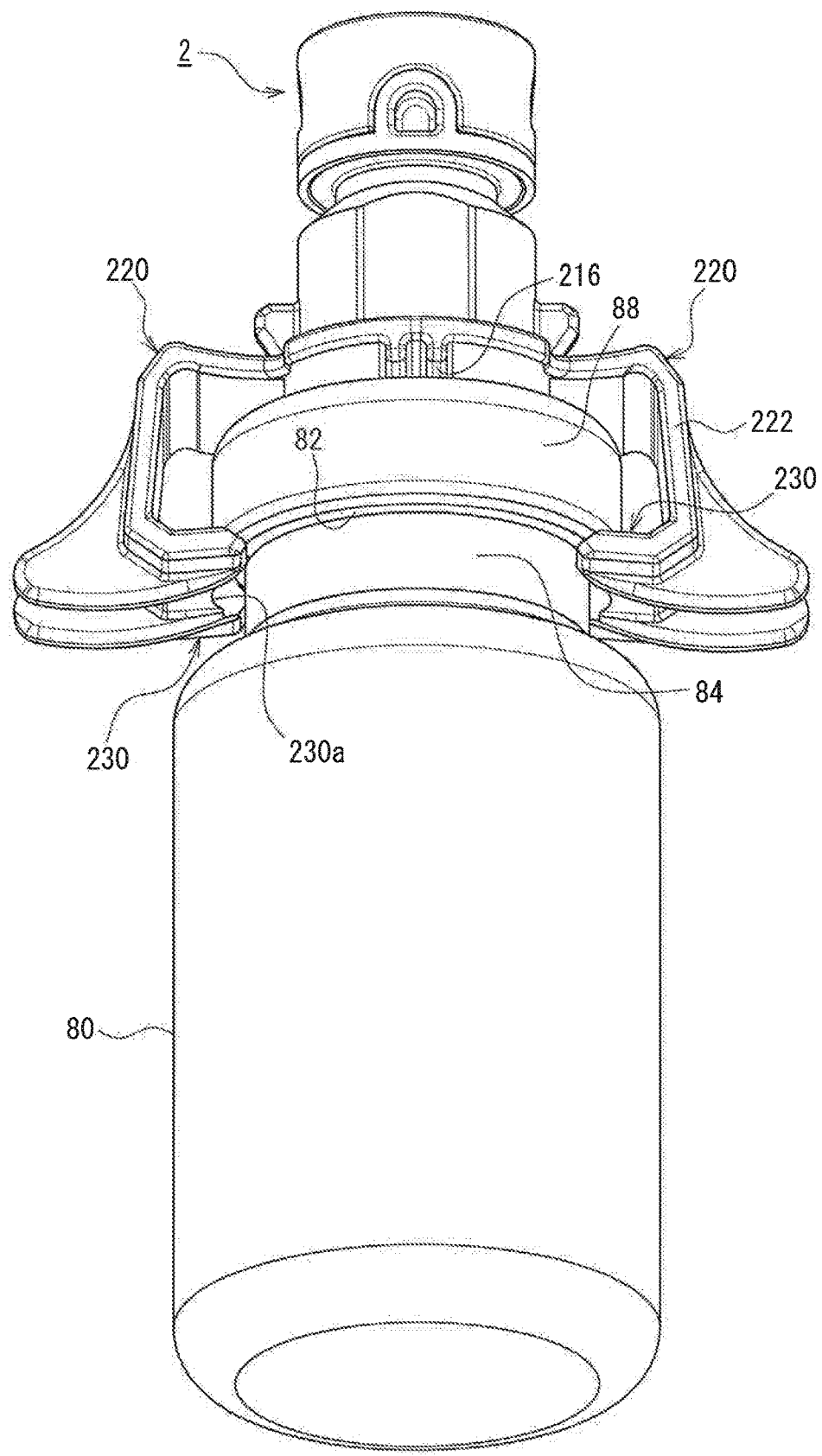
FIG. 11A is a perspective view showing a state of the adapter according to Embodiment 2 of the present invention connected to a vial bottle, seen from below.
Figure 11B:
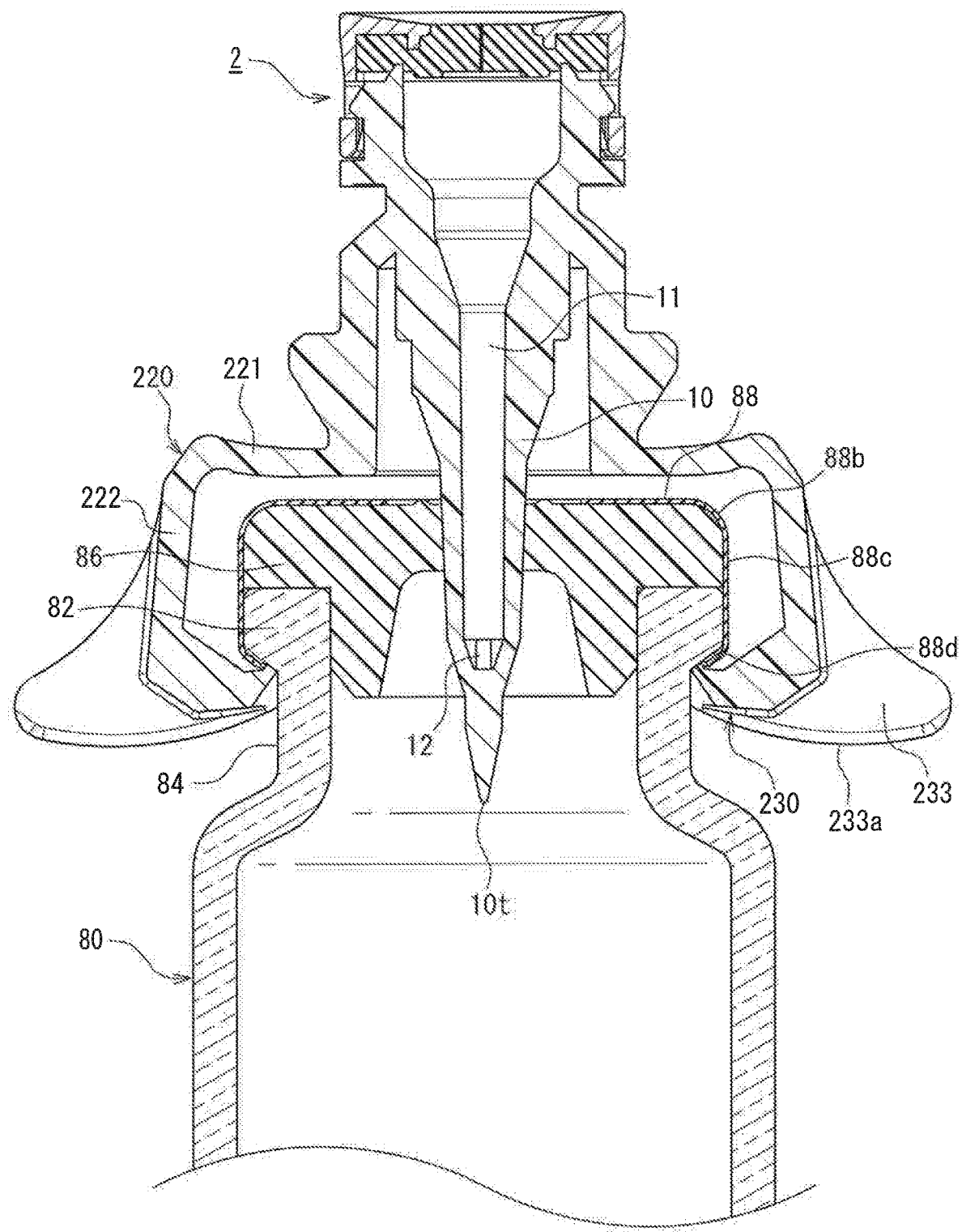
FIG. 11B is a cross-sectional view of FIG. 11A

Thus, as shown in FIGS. 11A and 11B, the adapter 2 can be connected to the vial bottle 80.

As shown in FIG. 11A, the claws 230 engage with the flange 82, which has an expanded diameter. Therefore, even if a pulling force or vibrations are applied to the adapter 2 and the vial bottle 80 in a direction in which the adapter 2 and the vial bottle 80 are separated from each other, the puncture needle 10 does not unintentionally come out of the plug member 86.

The constricted portion 84 of the vial bottle 80 is fitted into the recessed portions 230a of the claws 230. Therefore, although the number of claws 230 that the adapter 2 according to the present Embodiment 2 is only two, even if an external force or vibrations are applied, the adapter 2 can be stably attached to the vial bottle 80 without being inclined relative to the vial bottle 80. Therefore, it is possible to avoid a situation in which the puncture needle 10 inclines, a narrow gap is created between the puncture needle 10 and a hole in the plug member 86 pierced by the puncture needle 10, and a drug in the vial bottle 80 leaks to the outside via the gap.

The protrusions 216 abuts against the upper surface of the plug member 86 or the upper surface of the cap 88. Therefore, it is possible to avoid a situation in which the engagement between the claws 230 and the flange 82 becomes unstable due to the arms 220 deforming as a result of the arms 220, especially the shoulder portions 221 thereof, hitting the plug member 86 or the cap 88. Also, it is possible to prevent the adapter 2 from inclining relative to the vial bottle 80.

As shown in FIG. 11B, the puncture needle 10 penetrates through the plug member 86, and the opening 12, which is formed near the leading end of the puncture needle 10, is exposed, below the plug member 86. Therefore, the flow channel 11 in the puncture needle 10 communicates with the inner cavity of the vial bottle 80.

The contour shape of each of the slidable portion 233a seen in a direction that is orthogonal to the central axis 2a (a direction that is orthogonal to the ribs 233) is an arc shape (see FIG. 9C) as with the slidable portions 33a of the adapter 1 according to Embodiment 1 (see FIG. 1C). Therefore, as with the adapter 1 according to Embodiment 1, the adapter 2 according to the present Embodiment 2 requires a smaller force when being connected to the vial bottle 80, compared to the conventional adapter 900. Also, the size range of vial bottles 80 to which the adapter 2 can be connected is large.

In the present Embodiment 2, in the same manner as described in Embodiment 1, the contour shape of each slidable portion 233a is not limited to an arc shape, and generally any shape that includes a smooth convex curve suffices to achieve the above-described effects.

The slidable portions 233a are provided on the thin plate-like ribs 233. With such a configuration, the contact areas of the slidable portions 233a and the cap 88 can be reduced, and the friction force therebetween can be reduced. Therefore, such a configuration is advantageous in that the force that is to be applied to the adapter 2 can be further reduced.

The ribs 33 in Embodiment 1 are provided along a plane that includes the central axis 1a, whereas the ribs 233 in the present Embodiment 2 are not provided along a plane that includes the central axis 2a, but along a plane that is parallel with the aforementioned plane. However, the distance from the plane that includes the central axis 2a to the ribs 233 is extremely small. Therefore, the present Embodiment 2 is substantially the same as the Embodiment 1 in terms of the above-described effects that can be achieved by the slidable portions provided on the ribs.

The above-described Embodiment 2 is merely an example. The present invention is not limited to the above-described Embodiment 2, and may be modified as appropriate. In particular, configurations other than the slidable portions 233a of the claws 230 can be modified in any manner.

For example, the shape of the arms 220 for which the claws 230 are provided may be modified in any manner. When the arms 220 are seen in a direction that is orthogonal to the central axis 2a (see FIG. 9C), the shoulder portions 221 and the suspended portions 222 may be inclined at any angle relative to the horizontal direction and the vertical direction. The arms 220 are not limited to a configuration in which a shoulder portion 221 and a suspended portion 222 are connected with a bent portion interposed therebetween. For example, the entirety of each arm may bend along a smooth curve. The top plate 215 that is substantially not deformable may be expanded in a horizontal direction to positions that correspond to the distal ends of the shoulder portions 221, and the arms may each be constituted by a member that has a strip shape (a substantially "I" like shape) extending downward from the outer peripheral edge of the top plate 215 so as to face the puncture needle 10. If this is the case, the portions that have the strip-like shape are elastically bendable.

The number of arms is not limited to two, and may be three or more. However, it is preferable that a plurality of arms are equiangularly located with respect to the central axis 1a.

The number of ribs 233 provided for one arm is not limited to two, and may be one, or three or more.

The number of claws 230 provided for one arm is not limited to one. For example, the claws 230 (i.e. the stopper plates 231) may be divided for each rib 233, and the same number of claws 230 as the ribs 233 may be provided for one arm.

The inclination of the stopper plates 231 of the claws 230 may be determined as desired. It is not essential that the stopper plates 231 are inclined relative to the horizontal direction, and may be parallel with the horizontal direction, for example. The stopper plates 231 may be omitted, and the claws may be constituted by only the ribs 233 (i.e. plate-like objects that each extend along a plane that is parallel with a plane that includes the central axis 1a).

It is not essential that the recessed portions 230a are provided in the leading ends 230t of the claws 230.

The configuration (e.g. the shape, position, and number) of the protrusions 216 provided on the lower surface of the top plate 215 can be determined as desired. For example, each protrusion 216 may be a semispherical convex object. Alternatively, ring-like, arc-like, or dot-like protrusion(s) that is/are arranged along a circle that is concentric with respect to the central axis 2a may be employed. The protrusions 216 may be provided on the arms 220 (especially on the shoulder portions 221 thereof). The protrusions 216 may be omitted.

The present Embodiment 2 is the same as the Embodiment 1 except for the above-described points. The descriptions for Embodiment 1 also apply to the present Embodiment 2.

In the above-described Embodiments 1 and 2, the arms 20 or 220 are indirectly supported by the base end portion 10b of the puncture needle 10 with the tubular portion 14 and the top plate 15 or 215 being interposed therebetween. However, the present invention is not limited to such a configuration. For example, the tubular portion 14 may be omitted, and the top plate 15 or 215 may be provided on the base end portion 10b of the puncture needle 10. If this is the case, the arms 20 or 220 are indirectly supported by the base end portion 10b of the puncture needle 10 with the top plate 15 or 215 being interposed therebetween. Alternatively, the top plate 15 or 215 may be omitted, and the arms 20 or 220 may be provided on the tubular portion 14. If this is the case, the arms 20 or 220 are indirectly supported by the base end portion 10b of the puncture needle 10 with the tubular portion 14 being interposed therebetween. Alternatively, the tubular portion 14 and the top plate 15 or 215 may be omitted, and the arms 20 or 220 may be provided on the base end portion 10b of the puncture needle 10. If this is the case, the arms 20 or 220 are directly supported by the base end portion 10b of the puncture needle 10. Alternatively, a member other than the tubular portion 14 and the top plates 15 and 215 may be interposed between the base end portion 10b of the puncture needle 10 and the arms 20 or 220. In this way, in the present invention, the arms only need to be supported by the base end portion 10b of the male member 10 regardless of whether the arms are supported indirectly or directly.

It is only necessary that at least a portion of each arm faces the puncture needle 10, and it is not necessary that the entirety of each arm faces the puncture needle 10.

The entirety of each arm may be elastically bendable, or only a portion of each arm may be elastically bendable. An elastically bendable portion of each arm can be set as desired.

In the present invention, "the slidable portion" is a portion that slides on a predetermined portion (the upper edge 88b in the above-described Embodiments 1 and 2) of the female connector during a process in which the adapter is connected to the female connector, and is a portion that is configured to bend and move an arm such that a claw moves away from the puncture needle, while sliding on a predetermined position of the female connector. Therefore, a portion of a claw (or a rib) that does not come into contact with the female connector during a process in which the adapter is connected to the female connector is not included in "the slidable portion", and the shape of such a portion can be determined as desired. Also, the slidable portion has a predetermined area, and while the slidable portion slides on a predetermined portion of the female connector, a portion of the slidable portion that comes into contact with the predetermined portion of the female connector changes over time. Therefore, a leading end of a claw that is provided at or adjacent to the terminal end of the slidable portion is generally not included in "the slidable portion" of the present invention because the leading end of a claw does not have a sufficient area in which a portion that comes into contact with the predetermined portion of the female connector changes over time during the process in which the adapter is connected to the female connector. "The slidable portion" is located outward of the leading end of a claw (a portion of the claw that is closest to the male member) (i.e. on the opposite side to the male member). Preferably, the leading end of a claw coincides with the inner end of the slidable portion (a portion of the slidable portion that is closest to the male member). Therefore, the slidable portion preferably extends outward from the leading end of a claw.

A female connector to which the adapter according to the present invention is connected is not limited to the vial bottle 80. The adapter according to the present invention can be connected to any female connector that is provided with a flange that has an expanded diameter around the mouth (the opening) that is sealed by a rubber plug, in the same manner as in the case of the vial bottle 80. Such a female connector may be provided at one end of a flexible tube, for example, or the port of a container that stores a drug solution (a bottle-like container that has shape retention properties, a pouch-like container (a bag) that does not have shape retention properties, or the like). Alternatively, the female connector may be a so-called needleless port that is provided with an elastic partition member 42 as with the connector 40.

The configuration of the male member that is to be inserted into the female connector may be modified as appropriate according to the type of female connector.

Two independent flow channels may be formed in the puncture needle 10. If this is the case, one of the flow channels can be used as a liquid flow channel through which a liquid flows to/from the vial bottle 80. The other flow channel can be used as an air flow channel through which air flows so that changes in the pressure in the vial bottle 80 can be reduced when a liquid flows into/out of the vial bottle 80.

Two or more openings 12 that communicate with the flow channel 11 may be provided.

The male member may be provided with a male Luer fitting that has a so-called tubular shape without a sharp leading end, instead of the puncture needle 10. The male Luer fitting may be preferably employed when the female connector is a needleless port.

The liquid that flows through the flow channel in the male member may be a drug solution or any kind of liquid other than a drug solution.

The configuration of the connector 40 is not limited to the needleless port shown in the above-described Embodiment 1 and 2. For example, the connector 40 may be a well-known connector that is provided with a tapered surface. Alternatively, a flexible tube such as an infusion set may be directly connected to the adapter without the connector 40 so as to communicate with the flow channel 11.

INDUSTRIAL APPLICABILITY

The field in which the present invention can be used is not limited, and the present invention can be widely used in the fields of medicine, food, chemistry, etc., and in particular, the present invention can be preferably used in the field of medicine. In particular, the present invention can be preferably used as an adapter that is to be connected to a female connector from/to which a powerful drug such as an anti-cancer drug is transferred.

DESCRIPTION OF REFERENCE NUMERALS 1, 2 Adapter
1a, 2a Central Axis
10 Puncture Needle (Male Member)
10b Base End Portion of Puncture Needle
20, 220 Arm 30, 230 Claw
33, 233 Rib
33a, 233a Slidable Portion
80 Vial Bottle
82 Flange
86 Plug Member

The invention claimed is:

1. An adapter comprising: a male member; an arm that faces the male member; and a claw that is provided on the arm so as to protrude toward the male member,
  wherein the adapter is configured to be connected to a female connector with the male member being inserted into the female connector and the claw engaging with the female connector,
  the arm is elastically deformable so that the claw can move away from the male member,
  the claw includes a slidable portion that slides on the female connector during a process in which the adapter is connected to the female connector,
  the slidable portion is configured to move the claw away from the male member while the slidable portion slides on the female connector,
  a contour shape of the slidable portion seen in a direction that is orthogonal to a central axis that passes through the male member includes a smooth convex curve, and
  the slidable portion is provided on a rib that is a thin plate that extends along a plane that includes the central axis, or along a plane that is parallel with a plane that includes the central axis.

2. The adapter according to claim 1, wherein the smooth convex curve is an arc or a portion of an ellipse.

3. The adapter according to claim 1, wherein the male member is a puncture needle that has a sharp leading end.

4. The adapter according to claim 1,
  wherein the female connector includes a plug member of a vial bottle, and
  the claw engages with a flange that has an expanded diameter and surrounds the mouth of the vial bottle.

* * * * *